United States Patent [19]

Montelaro et al.

[11] Patent Number: 5,714,577
[45] Date of Patent: Feb. 3, 1998

[54] ANTIMICROBIAL PEPTIDES

[75] Inventors: Ronald C. Montelaro; Sarah Burroughs Tencza; Timothy A. Mietzner, all of Pittsburgh, Pa.

[73] Assignee: University of Pittsburgh, Pittsburgh, Pa.

[21] Appl. No.: 786,748

[22] Filed: Jan. 24, 1997

Related U.S. Application Data

[60] Provisional application No. 60/010,634, Jan. 26, 1996.

[51] Int. Cl.$^6$ .............................. A61K 38/16; C07K 14/00
[52] U.S. Cl. .............................. 530/324; 530/326; 530/327; 514/2; 514/12; 514/13; 514/14
[58] Field of Search .............................. 514/2, 12, 13, 514/14; 530/324, 326, 327

[56] References Cited

FOREIGN PATENT DOCUMENTS 0273716  7/1988  European Pat. Off. .

OTHER PUBLICATIONS

Miller et al., AIDS Res. Hum. Retroviruses 9:1057, 1993.
Miller et al., AIDS Res. Hum. Retroviruses 7:511, 1991.
Srinivas et al., J. Biol. Chem. 267:7121, 1992.
Arroyo et al., J. Virol. 69:4095, 1995.
Tencza et al., AIDS Res. Hum. Retroviruses 13:263, 1997.
Zhong et al. Int. J. Pept. Prot. Res., 45:337, 1995.
Srinivas et al., J. Biol. Chem. 268:22895, 1993.
Chernomordik et al., J. Virol. 68:7115, 1994.
Gawrish et al., Biochemistry 32:3112, 1993.
Srinivas et al., AIDS Res. Hum. Retroviruses 10:1489, 1994.
Tencza et al., J. Virol. 69:5199, 1995.
Rushlow et al., Virology 155:309, 1986.
Habermann et al., Science 177:314, 1972.
Miller et al., Virology 196:89, 1993.
Fontenot et al., Peptide Research 45:19, 1991.
Zhang et al., Proc. Natl. Acad. Sci. USA 93:12519, 1996.
Yuan et al., Biochemistry 34:10690, 1995.
Venable et al., AIDS Res. Hum. Retroviruses 5:7, 1989.
Garnier et al., J. Mol. Biol. 120:97, 1978.
Eisenberg et al., Proc. Natl. Acad. Sci. U.S.A. 81:140, 1984.
Wild et al., Proc. Natl. Acad. Sci. USA 89:10537, 1992.
Moore et al., Peptide Research 7:265, 1994.
Chou et al., Biochemistry 13:222, 1974.
Eisenberg et al., J. Mol. Biol. 179:125, 1984.
Lehrer et al., Infect. Immun. 42:10, 1983.
Pearson et al., Antimicrob. Agents Chemother. 18:699, 1980.
Fujii et al., Protein Sci. 1:1454, 1992.
Eisenberg et al., Biopolymers 29:171, 1990.
Chernomordik, A. et al., An Amphipathic Peptide from the C–Terminal Region of the HIV Envelope Glycoprotein Causes Pore Formation in Membranes, *J. Virol.* 68, 7115–7123 (1994). see entire article.
Gawrisch et al., Interaction of Peptide Fragment 828–848 of the Envlope Glycoprotein of HIV with Lipid Bilayers, *Biochemistry* 32, 3112–3118 (1993). see entire article.
Koenig, B. et al., Effect of the conformation of a peptide from gp41 on binding and domain formation in model membranes, *Mol. Membrane Biol.* 12, 77–82 (1995). see entire article.
Ward, N. et al., Inhibition of protein kinase C by a synthetic peptide, Cancer Lett. 88, 37–40 (1995). see entire article.

*Primary Examiner*—Paula K. Hutzell
*Assistant Examiner*—Benet Prickril
*Attorney, Agent, or Firm*—Brumbaugh, Graves, Donohue & Raymond

[57] ABSTRACT

The invention is directed to antimicrobial peptides which correspond in sequence to selective amino acid sequences in viral transmembrane proteins. In particular, the proteins are derived from lentiviruses, primarily HIV and SIV. The peptides comprise arginine-rich sequences, which, when modeled for secondary structure, display a high amphipathicity and hydrophobic moment. They are highly inhibitory to microorganisms, while being significantly less active in regard to mammalian cells. As a result, the peptides of the invention may be defined as selective antimicrobial agents. The invention is also directed to antimicrobial peptides which are structural and functional analogs and homologs of the peptides and which exhibit selective inhibitory activity towards microorganisms. The invention is also directed to pharmaceutical compositions comprising the antimicrobial peptides of the invention and to methods for their use in inhibiting microbial growth and treatment of microbial infections.

10 Claims, 5 Drawing Sheets

SEQUENCE LISTING ( 1 ) GENERAL INFORMATION:

( i i i ) NUMBER OF SEQUENCES: 169

( 2 ) INFORMATION FOR SEQ ID NO:1:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:1:

```
Arg Val Ile Glu Val Val Gln Gly Ala Cys Arg Ala Ile Arg His Ile
 1               5                  10                  15

Pro Arg Arg Ile Arg Gln Gly Leu Glu Arg Ile Leu
                20                  25
```

( 2 ) INFORMATION FOR SEQ ID NO:2:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:2:

Tyr His Arg Leu Arg Asp Leu Leu Leu Ile Val Thr Arg Ile Val Glu
1               5                   10                  15

Leu Leu Gly Arg Arg
            20

( 2 ) INFORMATION FOR SEQ ID NO:3:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:3:

Asp Leu Trp Glu Thr Leu Arg Arg Gly Gly Arg Trp Ile Leu Ala Ile
1               5                   10                  15

Pro Arg Arg Ile Arg Gln Gly Leu Glu Leu Thr Leu
            20                  25

( 2 ) INFORMATION FOR SEQ ID NO:4:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:4:

Phe Leu Ile Arg Gln Leu Ile Arg Leu Leu Thr Trp Leu Phe Ser Asn
1               5                   10                  15

Cys Arg Thr Leu Leu Ser Arg Val Tyr
            20                  25

( 2 ) INFORMATION FOR SEQ ID NO:5:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:5:

Leu Leu Ser Arg Val Tyr Gln Ile Leu Gln Pro Ile Leu Gln Arg Leu
1               5                   10                  15

Ser Ala Thr Leu Gln Arg Ile Arg Glu Val Leu Arg
            20                  25

( 2 ) INFORMATION FOR SEQ ID NO:6:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:6:

Arg Ile Ala Gly Tyr Gly Leu Arg Gly Leu Ala Val Ile Ile Arg Ile

```
         1               5                    10                   15
Cys Ile Arg Gly Leu Asn Leu Ile Phe Glu Ile Ile Arg
               20                  25
```

( 2 ) INFORMATION FOR SEQ ID NO:7:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:7:

```
Arg Val Ile Glu Val Val Gln Gly Ala Cys Arg Ala Ile Arg His Ile
 1               5                   10                  15
Pro Arg Arg Ile Arg
              20
```

( 2 ) INFORMATION FOR SEQ ID NO:8:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:8:

```
Val Val Gln Gly Ala Cys Arg Ala Ile Arg His Ile Pro Arg Arg Ile
 1               5                   10                  15
Arg
```

( 2 ) INFORMATION FOR SEQ ID NO:9:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:9:

```
Gly Ala Cys Arg Ala Ile Arg His Ile Pro Arg Arg Ile Arg
 1               5                   10
```

( 2 ) INFORMATION FOR SEQ ID NO:10:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:10:

```
Arg Val Ile Arg Val Val Gln Gly Ala Cys Arg Ala Ile Arg His Ile
 1               5                   10                  15
Pro Arg Arg Ile Arg
              20
```

( 2 ) INFORMATION FOR SEQ ID NO:11:

( i ) SEQUENCE CHARACTERISTICS:
   ( A ) LENGTH: 21 amino acids
   ( B ) TYPE: amino acid
   ( C ) STRANDEDNESS: single
   ( D ) TOPOLOGY: linear ( i i ) MOLECULE TYPE: None ( x i ) SEQUENCE DESCRIPTION: SEQ ID NO:11:

Arg Val Ile Glu Val Val Arg Gly Ala Cys Arg Ala Ile Arg His Ile
 1               5                   10                  15

Pro Arg Arg Ile Arg
             20

( 2 ) INFORMATION FOR SEQ ID NO:12:

( i ) SEQUENCE CHARACTERISTICS:
   ( A ) LENGTH: 21 amino acids
   ( B ) TYPE: amino acid
   ( C ) STRANDEDNESS: single
   ( D ) TOPOLOGY: linear ( i i ) MOLECULE TYPE: None ( x i ) SEQUENCE DESCRIPTION: SEQ ID NO:12:

Arg Val Ile Glu Val Val Gln Gly Ile Cys Arg Ala Ile Arg His Ile
 1               5                   10                  15

Pro Arg Arg Ile Arg
             20

( 2 ) INFORMATION FOR SEQ ID NO:13:

( i ) SEQUENCE CHARACTERISTICS:
   ( A ) LENGTH: 21 amino acids
   ( B ) TYPE: amino acid
   ( C ) STRANDEDNESS: single
   ( D ) TOPOLOGY: linear ( i i ) MOLECULE TYPE: None ( x i ) SEQUENCE DESCRIPTION: SEQ ID NO:13:

Arg Val Ile Ser Val Val Gln Gly Ala Cys Arg Ala Ile Arg Arg Ile
 1               5                   10                  15

Pro Arg Arg Ile Arg
             20

( 2 ) INFORMATION FOR SEQ ID NO:14:

( i ) SEQUENCE CHARACTERISTICS:
   ( A ) LENGTH: 28 amino acids
   ( B ) TYPE: amino acid
   ( C ) STRANDEDNESS: single
   ( D ) TOPOLOGY: linear ( i i ) MOLECULE TYPE: None ( x i ) SEQUENCE DESCRIPTION: SEQ ID NO:14:

Arg Val Ile Arg Val Val Gln Gly Ala Cys Arg Ala Ile Arg His Ile
 1               5                   10                  15

Pro Arg Arg Ile Arg Gln Gly Leu Glu Arg Ile Leu
             20                  25

( 2 ) INFORMATION FOR SEQ ID NO:15:

( i ) SEQUENCE CHARACTERISTICS:
   ( A ) LENGTH: 28 amino acids
   ( B ) TYPE: amino acid
   ( C ) STRANDEDNESS: single ( D ) TOPOLOGY: linear ( i i ) MOLECULE TYPE: None ( x i ) SEQUENCE DESCRIPTION: SEQ ID NO:15:

Arg Val Ile Glu Val Val Arg Gly Ala Cys Arg Ala Ile Arg His Ile
1               5                   10                  15

Pro Arg Arg Ile Arg Gln Gly Leu Glu Arg Ile Leu
            20                  25

( 2 ) INFORMATION FOR SEQ ID NO:16:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:16:

Arg Val Ile Glu Val Val Gln Gly Ile Cys Arg Ala Ile Arg His Ile
1               5                   10                  15

Pro Arg Arg Ile Arg Gln Gly Leu Glu Arg Ile Leu
            20                  25

( 2 ) INFORMATION FOR SEQ ID NO:17:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:17:

Arg Val Ile Ser Val Val Gln Gly Ala Cys Arg Ala Ile Arg Arg Ile
1               5                   10                  15

Pro Arg Arg Ile Arg Gln Gly Leu Glu Arg Ile Leu
            20                  25

( 2 ) INFORMATION FOR SEQ ID NO:18:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:18:

Arg Val Ile Glu Val Val Gln Gly Ala Cys Arg Ala Ile Arg His Ile
1               5                   10                  15

Pro Arg Arg Ile Arg Gln Ile Leu Glu Arg Ile Leu
            20                  25

( 2 ) INFORMATION FOR SEQ ID NO:19:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:19:

Arg Val Ile Glu Val Val Gln Gly Ala Cys Arg Ala Ile Arg His Ile
 1               5                   10                      15
Pro Arg Arg Ile Arg Gln Gly Leu Arg Arg Ile Leu
                 20              25

( 2 ) INFORMATION FOR SEQ ID NO:20:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:20:

Arg Val Ile Arg Val Val Gln Gly Ala Cys Arg Ala Ile Arg His Ile
 1               5                   10                      15
Pro Arg Arg Ile Arg
                 20

( 2 ) INFORMATION FOR SEQ ID NO:21:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:21:

Arg Val Ile Glu Val Val Arg Gly Ala Cys Arg Ala Ile Arg His Ile
 1               5                   10                      15
Pro Arg Arg Ile Arg
                 20

( 2 ) INFORMATION FOR SEQ ID NO:22:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:22:

Arg Val Ile Glu Val Val Gln Gly Ile Cys Arg Ala Ile Arg His Ile
 1               5                   10                      15
Pro Arg Arg Ile Arg
                 20

( 2 ) INFORMATION FOR SEQ ID NO:23:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:23:

Arg Val Ile Glu Val Val Gln Gly Ala Cys Arg Ala Ile Arg Arg Ile
 1               5                   10                      15

Pro Arg Arg Ile Arg
            20

( 2 ) INFORMATION FOR SEQ ID NO:24:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:24:

Arg Val Ile Arg Val Val Gln Gly Ala Cys Arg Ala Ile Arg His Ile
 1               5                   10                      15
Pro Arg Arg Ile Arg Gln Gly Leu Glu Arg Ile Leu
            20                  25

( 2 ) INFORMATION FOR SEQ ID NO:25:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:25:

Arg Val Ile Glu Val Val Arg Gly Ala Cys Arg Ala Ile Arg His Ile
 1               5                   10                      15
Pro Arg Arg Ile Arg Gln Gly Leu Glu Arg Ile Leu
            20                  25

( 2 ) INFORMATION FOR SEQ ID NO:26:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:26:

Arg Val Ile Glu Val Val Gln Gly Ile Cys Arg Ala Ile Arg His Ile
 1               5                   10                      15
Pro Arg Arg Ile Arg Gln Gly Leu Glu Arg Ile Leu
            20                  25

( 2 ) INFORMATION FOR SEQ ID NO:27:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:27:

Arg Val Ile Glu Val Val Gln Gly Ala Cys Arg Ala Ile Arg Arg Ile
 1               5                   10                      15
Pro Arg Arg Ile Arg Gln Gly Leu Glu Arg Ile Leu
            20                  25

(2) INFORMATION FOR SEQ ID NO:28:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:28:

```
Val Val Arg Gly Ala Cys Arg Ala Ile Arg His Ile Pro Arg Arg Ile
 1           5                   10                  15
Arg
```

(2) INFORMATION FOR SEQ ID NO:29:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:29:

```
Val Val Gln Gly Ile Cys Arg Ala Ile Arg His Ile Pro Arg Arg Ile
 1           5                   10                  15
Arg
```

(2) INFORMATION FOR SEQ ID NO:30:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:30:

```
Val Val Gln Arg Ala Cys Arg Ala Ile Arg Arg Ile Pro Arg Arg Ile
 1           5                   10                  15
Arg
```

(2) INFORMATION FOR SEQ ID NO:31:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:31:

```
Val Val Arg Gly Ala Cys Arg Ala Ile Arg His Ile Pro Arg Arg Ile
 1           5                   10                  15
Arg Gly Leu Glu Arg Ile Leu
             20
```

(2) INFORMATION FOR SEQ ID NO:32:

(i) SEQUENCE CHARACTERISTICS:
        (A) LENGTH: 23 amino acids
        (B) TYPE: amino acid
        (C) STRANDEDNESS: single ( D ) TOPOLOGY: linear ( i i ) MOLECULE TYPE: None ( x i ) SEQUENCE DESCRIPTION: SEQ ID NO:32:

```
Val Val Gln Gly Ile Cys Arg Ala Ile Arg His Ile Pro Arg Arg Ile
 1               5                  10                  15

Arg Gly Leu Glu Arg Ile Leu
                20
```

( 2 ) INFORMATION FOR SEQ ID NO:33:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:33:

```
Val Val Gln Gly Ala Cys Arg Ala Ile Arg Arg Ile Pro Arg Arg Ile
 1               5                  10                  15

Arg Gly Leu Glu Arg Ile Leu
                20
```

( 2 ) INFORMATION FOR SEQ ID NO:34:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:34:

```
Gly Ala Cys Arg Ala Ile Arg Arg Ile Pro Arg Arg Ile Arg
 1               5                  10
```

( 2 ) INFORMATION FOR SEQ ID NO:35:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:35:

```
Gly Ala Cys Arg Ala Ile Arg Arg Ile Pro Arg Arg Ile Arg Gly Leu
 1               5                  10                  15

Glu Arg Ile Leu
                20
```

( 2 ) INFORMATION FOR SEQ ID NO:36:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:36:

```
Val Val Gln Arg Ala Cys Arg Ala Ile Arg His Ile Pro Arg Arg Ile
```

-continued

```
           1               5              10              15
Arg
```

( 2 ) INFORMATION FOR SEQ ID NO:37:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:37:

```
Arg  Ala  Cys  Arg  Ala  Ile  Arg  His  Ile  Pro  Arg  Arg  Ile  Arg
  1              5                        10
```

( 2 ) INFORMATION FOR SEQ ID NO:38:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:38:

```
Arg  Val  Ile  Arg  Val  Val  Arg  Gly  Ala  Cys  Arg  Ala  Ile  Arg  His  Ile
  1              5                        10                       15
Pro  Arg  Arg  Ile  Arg
             20
```

( 2 ) INFORMATION FOR SEQ ID NO:39:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:39:

```
Arg  Val  Ile  Arg  Val  Val  Arg  Gly  Ala  Cys  Arg  Ala  Ile  Arg  His  Ile
  1              5                        10                       15
Pro  Arg  Arg  Ile  Arg
             20
```

( 2 ) INFORMATION FOR SEQ ID NO:40:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:40:

```
Arg  Arg  Ile  Arg  His  Ile  Pro  Arg  Ala  Ile  Arg  Val  Val  Gln  Gly  Ala
  1              5                        10                       15
Cys
```

( 2 ) INFORMATION FOR SEQ ID NO:41:

( i ) SEQUENCE CHARACTERISTICS:

(A) LENGTH: 21 amino acids
(B) TYPE: amino acid
(C) STRANDEDNESS: single
(D) TOPOLOGY: linear (ii) MOLECULE TYPE: None (xi) SEQUENCE DESCRIPTION: SEQ ID NO:41:

Arg Ile Arg Arg Pro Ile His Arg Ile Ala Arg Cys Ala Gly Gln Val
1               5                   10                  15
Val Glu Ile Val Arg
            20

(2) INFORMATION FOR SEQ ID NO:42:

(i) SEQUENCE CHARACTERISTICS:
    (A) LENGTH: 28 amino acids
    (B) TYPE: amino acid
    (C) STRANDEDNESS: single
    (D) TOPOLOGY: linear (ii) MOLECULE TYPE: None (xi) SEQUENCE DESCRIPTION: SEQ ID NO:42:

Leu Ile Arg Glu Leu Gly Gln Arg Ile Arg Arg Pro Ile His Arg Ile
1               5                   10                  15
Ala Arg Cys Ala Gly Gln Val Val Glu Ile Val Arg
            20                  25

(2) INFORMATION FOR SEQ ID NO:43:

(i) SEQUENCE CHARACTERISTICS:
    (A) LENGTH: 28 amino acids
    (B) TYPE: amino acid
    (C) STRANDEDNESS: single
    (D) TOPOLOGY: linear (ii) MOLECULE TYPE: None (xi) SEQUENCE DESCRIPTION: SEQ ID NO:43:

Leu Ile Arg Glu Leu Gly Gln Arg Ile Arg Arg Pro Ile His Arg Ile
1               5                   10                  15
Ala Arg Cys Ala Gly Gln Val Val Arg Ile Val Arg
            20                  25

(2) INFORMATION FOR SEQ ID NO:44:

(i) SEQUENCE CHARACTERISTICS:
    (A) LENGTH: 28 amino acids
    (B) TYPE: amino acid
    (C) STRANDEDNESS: single
    (D) TOPOLOGY: linear (ii) MOLECULE TYPE: None (xi) SEQUENCE DESCRIPTION: SEQ ID NO:44:

Leu Ile Arg Glu Leu Gly Gln Arg Ile Arg Arg Pro Ile His Arg Ile
1               5                   10                  15
Ala Arg Cys Ala Gly Arg Val Val Glu Ile Val Arg
            20                  25

(2) INFORMATION FOR SEQ ID NO:45:

(i) SEQUENCE CHARACTERISTICS:
    (A) LENGTH: 28 amino acids
    (B) TYPE: amino acid
    (C) STRANDEDNESS: single
    (D) TOPOLOGY: linear ( i i ) MOLECULE TYPE: None ( x i ) SEQUENCE DESCRIPTION: SEQ ID NO:45:

Leu Ile Arg Glu Leu Gly Gln Arg Ile Arg Arg Pro Ile His Arg Ile
1               5                   10                  15
Ala Arg Cys Ile Gly Gln Val Val Glu Ile Val Arg
            20                  25

( 2 ) INFORMATION FOR SEQ ID NO:46:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:46:

Leu Ile Arg Glu Leu Gly Gln Arg Ile Arg Arg Pro Ile Arg Arg Ile
1               5                   10                  15
Ala Arg Cys Ala Gly Gln Val Val Glu Ile Val Arg
            20                  25

( 2 ) INFORMATION FOR SEQ ID NO:47:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:47:

Leu Ile Arg Glu Leu Gly Ile Arg Ile Arg Arg Pro Ile His Arg Ile
1               5                   10                  15
Ala Arg Cys Ala Gly Gln Val Val Glu Ile Val Arg
            20                  25

( 2 ) INFORMATION FOR SEQ ID NO:48:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:48:

Leu Ile Arg Arg Leu Gly Gln Arg Ile Arg Arg Pro Ile His Arg Ile
1               5                   10                  15
Ala Arg Cys Ala Gly Gln Val Val Glu Ile Val Arg
            20                  25

( 2 ) INFORMATION FOR SEQ ID NO:49:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:49:

Arg Ile Arg Arg Pro Ile His Arg Ile Ala Arg Cys Ala Gly Gln Val
1               5                   10                  15

Val Glu Ile Val Arg
            20

( 2 ) INFORMATION FOR SEQ ID NO:50:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:50:

Arg Ile Arg Arg Pro Ile His Arg Ile Ala Arg Cys Ala Gly Gln Val
1               5                   10                  15

Val Arg Ile Val Arg
            20

( 2 ) INFORMATION FOR SEQ ID NO:51:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:51:

Arg Ile Arg Arg Pro Ile His Arg Ile Ala Arg Cys Ala Gly Arg Val
1               5                   10                  15

Val Glu Ile Val Arg
            20

( 2 ) INFORMATION FOR SEQ ID NO:52:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:52:

Arg Ile Arg Arg Pro Ile His Arg Ile Ala Arg Cys Ile Gly Gln Val
1               5                   10                  15

Val Glu Ile Val Arg
            20

( 2 ) INFORMATION FOR SEQ ID NO:53:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:53:

Arg Ile Arg Arg Pro Ile Arg Arg Ile Ala Arg Cys Ala Gly Gln Val
1               5                   10                  15

Val Glu Ile Val Arg
            20

( 2 ) INFORMATION FOR SEQ ID NO:54:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:54:

Arg Ile Arg Arg Pro Ile His Arg Ile Ile Arg Cys Ile Gly Gln Val
 1               5                   10                  15

Val Arg Ile Val Arg
            20

( 2 ) INFORMATION FOR SEQ ID NO:55:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:55:

Arg Ile Arg Arg Pro Ile Arg Arg Ile Ile Arg Cys Ile Gly Gln Val
 1               5                   10                  15

Val Glu Ile Val Arg
            20

( 2 ) INFORMATION FOR SEQ ID NO:56:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:56:

Leu Ile Arg Glu Leu Gly Gln Arg Ile Arg Arg Pro Ile His Arg Ile
 1               5                   10                  15

Ala Arg Cys Ala Gly Gln Val Val
            20

( 2 ) INFORMATION FOR SEQ ID NO:57:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:57:

Leu Ile Arg Glu Leu Arg Gln Arg Ile Arg Arg Pro Ile His Arg Ile
 1               5                   10                  15

Ala Arg Cys Ala Arg Gln Val Val
            20

( 2 ) INFORMATION FOR SEQ ID NO:58:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:58:

```
Leu Ile Arg Glu Leu Gly Gln Arg Ile Arg Arg Pro Ile His Arg Ile
 1               5                  10                  15
Ala Arg Cys Ala Gly Arg Val Val
             20
```

( 2 ) INFORMATION FOR SEQ ID NO:59:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:59:

```
Leu Ile Arg Glu Leu Gly Gln Arg Ile Arg Arg Pro Ile His Arg Ile
 1               5                  10                  15
Ala Arg Cys Ile Gly Gln Val Val
             20
```

( 2 ) INFORMATION FOR SEQ ID NO:60:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:60:

```
Leu Ile Arg Glu Leu Gly Gln Arg Ile Arg Arg Pro Ile Arg Arg Ile
 1               5                  10                  15
Ala Arg Cys Ala Gly Gln Val Val
             20
```

( 2 ) INFORMATION FOR SEQ ID NO:61:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:61:

```
Leu Ile Arg Glu Leu Gly Ile Arg Ile Arg Arg Pro Ile His Arg Ile
 1               5                  10                  15
Ala Arg Cys Ala Gly Gln Val Val
             20
```

( 2 ) INFORMATION FOR SEQ ID NO:62:

( i ) SEQUENCE CHARACTERISTICS:
        ( A ) LENGTH: 24 amino acids ( B ) TYPE: amino acid
( C ) STRANDEDNESS: single
( D ) TOPOLOGY: linear ( i i ) MOLECULE TYPE: None ( x i ) SEQUENCE DESCRIPTION: SEQ ID NO:62:

Leu Ile Arg Arg Leu Gly Gln Arg Ile Arg Arg Pro Ile His Arg Ile
 1               5                   10                  15
Ala Arg Cys Ala Gly Gln Val Val
                20

( 2 ) INFORMATION FOR SEQ ID NO:63:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:63:

Leu Ile Arg Glu Leu Gly Gln Arg Ile Arg Arg Pro Ile His Arg Ile
 1               5                   10                  15
Ala Arg Cys Ala Gly
                20

( 2 ) INFORMATION FOR SEQ ID NO:64:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:64:

Leu Ile Arg Glu Leu Gly Gln Arg Ile Arg Arg Pro Ile His Arg Ile
 1               5                   10                  15
Ala Arg Cys Ala Arg
                20

( 2 ) INFORMATION FOR SEQ ID NO:65:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:65:

Leu Ile Arg Glu Leu Gly Gln Arg Ile Arg Arg Pro Ile His Arg Ile
 1               5                   10                  15
Ala Arg Cys Ala Ile
                20

( 2 ) INFORMATION FOR SEQ ID NO:66:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:66:

```
Leu Ile Arg Glu Leu Gly Gln Arg Ile Arg Arg Pro Ile His Arg Ile
 1               5                  10                  15
Ala Arg Cys Ile Gly
            20
```

( 2 ) INFORMATION FOR SEQ ID NO:67:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:67:

```
Leu Ile Arg Glu Leu Gly Gln Arg Ile Arg Arg Pro Ile Arg Arg Ile
 1               5                  10                  15
Ala Arg Cys Ala Gly
            20
```

( 2 ) INFORMATION FOR SEQ ID NO:68:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:68:

```
Leu Ile Arg Glu Leu Gly Ile Arg Ile Arg Arg Pro Ile His Arg Ile
 1               5                  10                  15
Ala Arg Cys Ala Gly
            20
```

( 2 ) INFORMATION FOR SEQ ID NO:69:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:69:

```
Leu Ile Arg Arg Leu Gly Gln Arg Ile Arg Arg Pro Ile His Arg Ile
 1               5                  10                  15
Ala Arg Cys Ala Gly
            20
```

( 2 ) INFORMATION FOR SEQ ID NO:70:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:70:

Arg Ala Ile Arg Arg Ala Ile Arg Gly Ala Pro Arg Ala Ile Leu
1               5                   10                  15

(2) INFORMATION FOR SEQ ID NO:71:

(i) SEQUENCE CHARACTERISTICS:
       (A) LENGTH: 19 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:71:

Arg Ala Ile Arg Arg Ala Ile Arg Gly Ala Pro Arg Ala Ile Leu Arg
1               5                   10                  15

Ala Ile Leu (2) INFORMATION FOR SEQ ID NO:72:

(i) SEQUENCE CHARACTERISTICS:
       (A) LENGTH: 28 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:72:

Lys Val Ile Glu Val Val Gln Gly Ala Cys Lys Ala Ile Lys His Ile
1               5                   10                  15

Pro Lys Lys Ile Lys Gln Gly Leu Glu Lys Ile Leu
            20                  25

(2) INFORMATION FOR SEQ ID NO:73:

(i) SEQUENCE CHARACTERISTICS:
       (A) LENGTH: 20 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:73:

Leu Trp Glu Thr Leu Arg Arg Gly Gly Arg Trp Ile Leu Ala Ile Pro
1               5                   10                  15

Arg Arg Ile Arg
            20

(2) INFORMATION FOR SEQ ID NO:74:

(i) SEQUENCE CHARACTERISTICS:
       (A) LENGTH: 28 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:74:

Asp Leu Trp Glu Thr Leu Arg Arg Ile Ile Arg Trp Ile Leu Ala Ile
1               5                   10                  15

Pro Arg Arg Ile Arg Gln Gly Leu Glu Leu Thr Leu
            20                  25

(2) INFORMATION FOR SEQ ID NO:75:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:75:

```
Asp Leu Trp Glu Thr Leu Arg Arg Gly Gly Arg Trp Ile Leu Ala Ile
 1               5                  10                      15
Pro Arg Arg Ile Arg Gln Gly Leu Glu Leu Cys Leu
            20                  25
```

( 2 ) INFORMATION FOR SEQ ID NO:76:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:76:

```
Asp Leu Trp Glu Thr Leu Arg Arg Gly Cys Arg Trp Ile Leu Ala Ile
 1               5                  10                      15
Pro Arg Arg Ile Arg Gln Gly Leu Glu Leu Thr Leu
            20                  25
```

( 2 ) INFORMATION FOR SEQ ID NO:77:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:77:

```
Asp Leu Trp Glu Thr Leu Arg Arg Ile Ile Arg Trp Ile Leu Ala Ile
 1               5                  10                      15
Pro Arg Arg Ile Arg Gln Gly Leu Glu Leu Cys Leu
            20                  25
```

( 2 ) INFORMATION FOR SEQ ID NO:78:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:78:

```
Leu Trp Glu Thr Leu Arg Arg Gly Gly Arg Trp Ile Leu Ala Ile Pro
 1               5                  10                      15
Arg Arg Ile Arg Gln Gly Leu Glu Leu Thr Leu
            20                  25
```

( 2 ) INFORMATION FOR SEQ ID NO:79:

( i ) SEQUENCE CHARACTERISTICS:
        ( A ) LENGTH: 27 amino acids
        ( B ) TYPE: amino acid ( C ) STRANDEDNESS: single
( D ) TOPOLOGY: linear ( i i ) MOLECULE TYPE: None ( x i ) SEQUENCE DESCRIPTION: SEQ ID NO:79:

Leu Trp Glu Thr Leu Arg Arg Gly Gly Arg Trp Ile Leu Ala Ile Pro
1               5                   10                  15

Arg Arg Ile Arg Gln Gly Leu Glu Leu Cys Leu
            20                  25

( 2 ) INFORMATION FOR SEQ ID NO:80:

( i ) SEQUENCE CHARACTERISTICS:
( A ) LENGTH: 27 amino acids
( B ) TYPE: amino acid
( C ) STRANDEDNESS: single
( D ) TOPOLOGY: linear ( i i ) MOLECULE TYPE: None ( x i ) SEQUENCE DESCRIPTION: SEQ ID NO:80:

Leu Trp Glu Thr Leu Arg Arg Gly Cys Arg Trp Ile Leu Ala Ile Pro
1               5                   10                  15

Arg Arg Ile Arg Gln Gly Leu Glu Leu Thr Leu
            20                  25

( 2 ) INFORMATION FOR SEQ ID NO:81:

( i ) SEQUENCE CHARACTERISTICS:
( A ) LENGTH: 27 amino acids
( B ) TYPE: amino acid
( C ) STRANDEDNESS: single
( D ) TOPOLOGY: linear ( i i ) MOLECULE TYPE: None ( x i ) SEQUENCE DESCRIPTION: SEQ ID NO:81:

Leu Trp Arg Thr Leu Arg Arg Gly Gly Arg Trp Ile Leu Ala Ile Pro
1               5                   10                  15

Arg Arg Ile Arg Gln Gly Leu Glu Leu Thr Leu
            20                  25

( 2 ) INFORMATION FOR SEQ ID NO:82:

( i ) SEQUENCE CHARACTERISTICS:
( A ) LENGTH: 27 amino acids
( B ) TYPE: amino acid
( C ) STRANDEDNESS: single
( D ) TOPOLOGY: linear ( i i ) MOLECULE TYPE: None ( x i ) SEQUENCE DESCRIPTION: SEQ ID NO:82:

Leu Trp Glu Thr Leu Arg Arg Gly Gly Arg Trp Ile Leu Ala Ile Pro
1               5                   10                  15

Arg Arg Ile Arg Gln Gly Leu Arg Leu Thr Leu
            20                  25

( 2 ) INFORMATION FOR SEQ ID NO:83:

( i ) SEQUENCE CHARACTERISTICS:
( A ) LENGTH: 27 amino acids
( B ) TYPE: amino acid
( C ) STRANDEDNESS: single
( D ) TOPOLOGY: linear ( i i ) MOLECULE TYPE: None ( x i ) SEQUENCE DESCRIPTION: SEQ ID NO:83:

Leu Trp Glu Thr Leu Arg Arg Gly Gly Arg Trp Ile Leu Ala Ile Pro
 1               5                   10                  15

Arg Arg Ile Arg Arg Gly Leu Glu Leu Thr Leu
            20                  25

( 2 ) INFORMATION FOR SEQ ID NO:84:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:84:

Leu Trp Glu Thr Leu Arg Arg Gly Gly Arg Trp Ile Leu Ala Ile Pro
 1               5                   10                  15

Arg Arg Ile Arg Arg Gln Ile Glu Leu Thr Leu
            20                  25

( 2 ) INFORMATION FOR SEQ ID NO:85:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:85:

Leu Trp Glu Leu Leu Arg Arg Gly Gly Arg Trp Ile Leu Ala Ile Pro
 1               5                   10                  15

Arg Arg Ile Arg Gln Gly Leu Glu Leu Thr Leu
            20                  25

( 2 ) INFORMATION FOR SEQ ID NO:86:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:86:

Leu Trp Arg Leu Leu Arg Arg Gly Gly Arg Trp Ile Leu Ala Ile Pro
 1               5                   10                  15

Arg Arg Ile Arg Gln Gly Leu Glu Leu Thr Leu
            20                  25

( 2 ) INFORMATION FOR SEQ ID NO:87:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:87:

Asp Leu Trp Glu Thr Leu Arg Arg Ile Ile Arg Trp Ile Leu Ala Ile

Pro Arg Arg Ile Arg
          20

( 2 ) INFORMATION FOR SEQ ID NO:88:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:88:

Asp Leu Trp Glu Thr Leu Arg Arg Gly Gly Arg Trp Ile Leu Ala Ile
 1               5                   10                  15
Pro Arg Arg Ile Arg
          20

( 2 ) INFORMATION FOR SEQ ID NO:89:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:89:

Asp Leu Trp Glu Thr Leu Arg Arg Gly Cys Arg Trp Ile Leu Ala Ile
 1               5                   10                  15
Pro Arg Arg Ile Arg
          20

( 2 ) INFORMATION FOR SEQ ID NO:90:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:90:

Leu Trp Glu Thr Leu Arg Arg Gly Gly Arg Trp Ile Leu Ala Ile Pro
 1               5                   10                  15
Arg Arg Ile Arg
          20

( 2 ) INFORMATION FOR SEQ ID NO:91:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:91:

Leu Trp Glu Thr Leu Arg Arg Ile Ile Arg Trp Ile Leu Ala Ile Pro
 1               5                   10                  15
Arg Arg Ile Arg
          20

( 2 ) INFORMATION FOR SEQ ID NO:92:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:92:

```
Leu Trp Glu Thr Leu Arg Arg Gly Cys Arg Trp Ile Leu Ala Ile Pro
 1               5                   10                  15
Arg Arg Ile Arg
            20
```

( 2 ) INFORMATION FOR SEQ ID NO:93:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:93:

```
Leu Trp Glu Thr Leu Arg Arg Gly Gly Arg Trp Ile Leu Ala Ile Pro
 1               5                   10                  15
Arg Arg Ile Arg
            20
```

( 2 ) INFORMATION FOR SEQ ID NO:94:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:94:

```
Leu Trp Glu Thr Leu Arg Arg Gly Cys Arg Trp Ile Leu Ala Ile Pro
 1               5                   10                  15
Arg Arg Ile Arg
            20
```

( 2 ) INFORMATION FOR SEQ ID NO:95:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:95:

```
Leu Trp Glu Thr Leu Arg Arg Ile Ile Arg Trp Ile Leu Ala Ile Pro
 1               5                   10                  15
Arg Arg Ile Arg
            20
```

( 2 ) INFORMATION FOR SEQ ID NO:96:

5,714,577

71

72

-continued ( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:96:

Leu Trp Glu Leu Leu Arg Arg Gly Gly Arg Trp Ile Leu Ala Ile Pro
 1               5                   10                  15

Arg Arg Ile Arg
            20

( 2 ) INFORMATION FOR SEQ ID NO:97:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:97:

Leu Trp Arg Leu Leu Arg Arg Gly Gly Arg Trp Ile Leu Ala Ile Pro
 1               5                   10                  15

Arg Arg Ile Arg
            20

( 2 ) INFORMATION FOR SEQ ID NO:98:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:98:

Leu Arg Arg Gly Gly Arg Trp Ile Leu Ala Ile Pro Arg Arg Ile Arg
 1               5                   10                  15

( 2 ) INFORMATION FOR SEQ ID NO:99:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:99:

Leu Trp Glu Thr Leu Arg Arg Gly Gly Arg Trp Ile Leu Ala Ile Pro
 1               5                   10                  15

Arg Ala Ile Leu
            20

( 2 ) INFORMATION FOR SEQ ID NO:100:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:100:

Leu Arg Arg Gly Gly Arg Trp Ile Leu Ala Ile Pro Arg Ala Ile Leu
 1               5                       10                      15

( 2 ) INFORMATION FOR SEQ ID NO:101:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:101:

Leu Trp Glu Thr Leu Arg Arg Gly Gly Arg Trp Ile Leu Ala Ile Pro
 1               5                       10                      15

Arg Glu Ile Leu
            20

( 2 ) INFORMATION FOR SEQ ID NO:102:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:102:

Leu Arg Arg Gly Gly Arg Trp Ile Leu Ala Ile Pro Arg Glu Ile Leu
 1               5                       10                      15

( 2 ) INFORMATION FOR SEQ ID NO:103:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:103:

Trp Ile Leu Ala Ile Pro Arg Arg Ile Arg Gly Gly Arg Leu Trp Glu
 1               5                       10                      15

Thr Leu ( 2 ) INFORMATION FOR SEQ ID NO:104:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:104:

Trp Glu Thr Leu Pro Arg Arg Ile Arg Gly Gly Arg Leu Trp Ile Leu
 1               5                       10                      15

Ala Ile ( 2 ) INFORMATION FOR SEQ ID NO:105:

( i ) SEQUENCE CHARACTERISTICS:
  ( A ) LENGTH: 20 amino acids
  ( B ) TYPE: amino acid
  ( C ) STRANDEDNESS: single
  ( D ) TOPOLOGY: linear ( i i ) MOLECULE TYPE: None ( x i ) SEQUENCE DESCRIPTION: SEQ ID NO:105:

Arg Ile Arg Arg Pro Ile Ala Leu Ile Trp Arg Gly Gly Arg Arg Leu
1               5                   10                  15
Thr Glu Trp Leu
            20

( 2 ) INFORMATION FOR SEQ ID NO:106:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:106:

Asp Leu Trp Glu Thr Leu Lys Lys Gly Gly Arg Trp Ile Leu Ala Ile
1               5                   10                  15
Pro Arg Arg Ile Lys Gln Gly Leu Glu Leu Thr Leu
            20                  25

( 2 ) INFORMATION FOR SEQ ID NO:107:

( i ) SEQUENCE CHARACTERISTICS:
    ( A ) LENGTH: 27 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:107:

Leu Trp Glu Thr Leu Gly Arg Val Gly Arg Trp Val Leu Ala Ile Pro
1               5                   10                  15
Arg Arg Ile Arg Gln Gly Leu Glu Leu Ala Leu
            20                  25

( 2 ) INFORMATION FOR SEQ ID NO:108:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:108:

Tyr His Arg Leu Arg Arg Leu Leu Leu Ile Val Thr Arg Ile Val Glu
1               5                   10                  15
Leu Leu Gly Arg Arg
            20

( 2 ) INFORMATION FOR SEQ ID NO:109:

( i ) SEQUENCE CHARACTERISTICS:
    ( A ) LENGTH: 21 amino acids
    ( B ) TYPE: amino acid
    ( C ) STRANDEDNESS: single (D) TOPOLOGY: linear (ii) MOLECULE TYPE: None (xi) SEQUENCE DESCRIPTION: SEQ ID NO:109:

Tyr His Arg Leu Arg Asp Leu Leu Arg Ile Val Thr Arg Ile Val Glu
 1               5                   10                  15

Leu Leu Gly Arg Arg
            20

(2) INFORMATION FOR SEQ ID NO:110:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:110:

Tyr His Arg Leu Arg Asp Leu Leu Leu Ile Val Arg Arg Ile Val Glu
 1               5                   10                  15

Leu Leu Gly Arg Arg
            20

(2) INFORMATION FOR SEQ ID NO:111:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:111:

Tyr His Arg Leu Arg Asp Leu Leu Leu Ile Val Thr Arg Ile Val Arg
 1               5                   10                  15

Leu Leu Gly Arg Arg
            20

(2) INFORMATION FOR SEQ ID NO:112:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:112:

Tyr His Arg Leu Arg Asp Leu Leu Leu Ile Val Thr Arg Ile Val Cys
 1               5                   10                  15

Leu Leu Gly Arg Arg
            20

(2) INFORMATION FOR SEQ ID NO:113:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: None ( x i ) SEQUENCE DESCRIPTION: SEQ ID NO:113:

Tyr His Arg Leu Arg Asp Leu Leu Leu Ile Val Arg Arg Ile Val Cys
 1               5                   10                  15
Leu Leu Gly Arg Arg
            20

( 2 ) INFORMATION FOR SEQ ID NO:114:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:114:

Tyr His Arg Leu Leu Arg Asp Leu Leu Ile Val Thr Arg Ile Val Glu
 1               5                   10                  15
Leu Leu Gly Arg Arg
            20

( 2 ) INFORMATION FOR SEQ ID NO:115:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:115:

Tyr His Arg Leu Arg Arg Leu Leu Leu Ile Val Thr Arg Ile Val Glu
 1               5                   10                  15
Leu Leu ( 2 ) INFORMATION FOR SEQ ID NO:116:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:116:

Tyr His Arg Leu Arg Asp Leu Leu Arg Ile Val Thr Arg Ile Val Glu
 1               5                   10                  15
Leu Leu ( 2 ) INFORMATION FOR SEQ ID NO:117:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:117:

Tyr His Arg Leu Arg Asp Leu Leu Leu Ile Val Arg Arg Ile Val Glu
 1               5                   10                  15
Leu Leu ( 2 ) INFORMATION FOR SEQ ID NO:118:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:118:

```
Tyr His Arg Leu Arg Asp Leu Leu Leu Ile Val Thr Arg Ile Val Arg
 1               5                   10                  15
Leu Leu
```

( 2 ) INFORMATION FOR SEQ ID NO:119:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:119:

```
Tyr His Arg Leu Arg Asp Leu Leu Leu Ile Val Thr Arg Ile Val Cys
 1               5                   10                  15
Leu Leu
```

( 2 ) INFORMATION FOR SEQ ID NO:120:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:120:

```
Tyr His Arg Leu Arg Asp Leu Leu Leu Ile Val Arg Arg Ile Val Cys
 1               5                   10                  15
Leu Leu
```

( 2 ) INFORMATION FOR SEQ ID NO:121:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:121:

```
Tyr His Arg Leu Leu Arg Asp Leu Leu Ile Val Thr Arg Ile Val Glu
 1               5                   10                  15
Leu Leu
```

( 2 ) INFORMATION FOR SEQ ID NO:122:

( i ) SEQUENCE CHARACTERISTICS:
        ( A ) LENGTH: 18 amino acids
        ( B ) TYPE: amino acid
        ( C ) STRANDEDNESS: single (D) TOPOLOGY: linear (ii) MOLECULE TYPE: None (xi) SEQUENCE DESCRIPTION: SEQ ID NO:122:

```
Tyr His Arg Leu Arg Asp Leu Leu Leu Ile Val Thr Arg Ile Val Glu
 1               5                  10                  15
Leu Leu
```

(2) INFORMATION FOR SEQ ID NO:123:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:123:

```
Arg Arg Gly Leu Leu Glu Val Ile Arg Thr Val Ile Leu Pro Arg Arg
 1               5                  10                  15
Leu Leu Asp Arg Leu
             20
```

(2) INFORMATION FOR SEQ ID NO:124:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:124:

```
Tyr His Arg Leu Arg Asp Leu Ala Leu Ile Val Thr Arg Ile Val Glu
 1               5                  10                  15
Leu Leu
```

(2) INFORMATION FOR SEQ ID NO:125:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:125:

```
Arg Arg Gly Leu Leu Arg Val Ile Arg Thr Val Ile Leu Ala Leu Asp
 1               5                  10                  15
Ile Leu
```

(2) INFORMATION FOR SEQ ID NO:126:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:126:

```
Arg Arg Gly Leu Leu Glu Val Ile Arg Thr Val Ile Leu Leu Leu Asp
```

```
            1               5                  10                 15
Arg Leu Arg His Tyr
             20
```

( 2 ) INFORMATION FOR SEQ ID NO:127:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:127:

```
Arg Arg Gly Leu Leu Glu Val Ile Arg Thr Val Ile Leu Ala Leu Asp
 1               5                  10                 15
Arg Leu Arg His Tyr
             20
```

( 2 ) INFORMATION FOR SEQ ID NO:128:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:128:

```
Arg Arg Gly Leu Leu Glu Val Ile Arg Thr Val Ile Leu Ala Leu Asp
 1               5                  10                 15
Arg Leu
```

( 2 ) INFORMATION FOR SEQ ID NO:129:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:129:

```
Tyr His Arg Leu Arg Asp Leu Leu Leu Ile Val Cys Arg Ile Val Glu
 1               5                  10                 15
Leu Leu
```

( 2 ) INFORMATION FOR SEQ ID NO:130:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:130:

```
Tyr His Arg Leu Arg Asp Leu Leu Leu Ile Val Cys Arg Ile Val Glu
 1               5                  10                 15
Leu Leu Gly Arg Arg
             20
```

( 2 ) INFORMATION FOR SEQ ID NO:131:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:131:

```
Tyr His Arg Leu Arg Asp Leu Leu Leu Ile Val Thr Arg Ile Val Glu
 1               5                  10                  15
Leu Leu Gly Arg Arg
             20
```

( 2 ) INFORMATION FOR SEQ ID NO:132:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:132:

```
Arg Arg Gly Leu Leu Glu Val Ile Arg Cys Val Ile Leu Leu Leu Asp
 1               5                  10                  15
Arg Leu
```

( 2 ) INFORMATION FOR SEQ ID NO:133:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:133:

```
Arg Arg Gly Leu Leu Arg Val Ile Arg Thr Val Ile Leu Leu Leu Asp
 1               5                  10                  15
Arg Leu
```

( 2 ) INFORMATION FOR SEQ ID NO:134:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:134:

```
Arg Arg Gly Leu Leu Glu Val Ile Arg Thr Val Ile Leu Leu Leu Arg
 1               5                  10                  15
Arg Leu
```

( 2 ) INFORMATION FOR SEQ ID NO:135:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:135:

Arg Arg Gly Leu Leu Glu Val Ile Arg Cys Val Ile Leu Leu Leu Asp
1               5                   10                  15
Arg Leu Arg His Tyr
            20

( 2 ) INFORMATION FOR SEQ ID NO:136:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:136:

Arg Arg Gly Leu Leu Arg Val Ile Arg Thr Val Ile Leu Leu Leu Asp
1               5                   10                  15
Arg Leu Arg His Tyr
            20

( 2 ) INFORMATION FOR SEQ ID NO:137:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:137:

Arg Arg Gly Leu Leu Glu Val Ile Arg Thr Val Ile Leu Leu Leu Arg
1               5                   10                  15
Arg Leu Arg His Tyr
            20

( 2 ) INFORMATION FOR SEQ ID NO:138:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:138:

Tyr His Lys Leu Lys Leu Leu Leu Ile Val Thr Lys Ile Val Glu Leu
1               5                   10                  15
Leu Gly Lys Lys
            20

( 2 ) INFORMATION FOR SEQ ID NO:139:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:139:

Phe Leu Ile Arg Gln Leu Ile Arg Gln Leu Leu Thr Trp Gln Pro Ile
1               5                   10                  15

Leu Gln Tyr Ile Leu Gln
            20

( 2 ) INFORMATION FOR SEQ ID NO:140:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:140:

Phe Leu Ile Arg Gln Leu Ile Arg Leu Leu Thr Trp Leu Phe Ser Asn
1               5                   10                  15

Cys Arg Thr Leu Leu Ser Glu Val Tyr
            20                  25

( 2 ) INFORMATION FOR SEQ ID NO:141:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:141:

Phe Leu Ile Arg Gln Leu Ile Arg Leu Leu Thr Trp Leu Phe Ser Asn
1               5                   10                  15

Cys Arg Thr Leu Leu
            20

( 2 ) INFORMATION FOR SEQ ID NO:142:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:142:

Leu Leu Thr Arg Cys Asn Ser Phe Leu Trp Thr Leu Leu Arg Ile Leu
1               5                   10                  15

Gln Arg Ile Leu Phe
            20

( 2 ) INFORMATION FOR SEQ ID NO:143:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:143:

Phe Leu Ile Arg Gln Leu Ile Arg Leu Leu Thr Trp Leu Phe Pro Asn
1               5                   10                  15

Cys Arg Thr Leu Leu Ser Arg Val Tyr
                20                  25

(2) INFORMATION FOR SEQ ID NO:144:

(i) SEQUENCE CHARACTERISTICS:
      (A) LENGTH: 25 amino acids
      (B) TYPE: amino acid
      (C) STRANDEDNESS: single
      (D) TOPOLOGY: linear (ii) MOLECULE TYPE: None (xi) SEQUENCE DESCRIPTION: SEQ ID NO:144:

Tyr Val Arg Ser Leu Leu Thr Arg Cys Asn Ser Phe Leu Trp Thr Leu
 1               5                  10                  15

Leu Arg Ile Leu Gln Arg Ile Leu Phe
                20                  25

(2) INFORMATION FOR SEQ ID NO:145:

(i) SEQUENCE CHARACTERISTICS:
      (A) LENGTH: 25 amino acids
      (B) TYPE: amino acid
      (C) STRANDEDNESS: single
      (D) TOPOLOGY: linear (ii) MOLECULE TYPE: None (xi) SEQUENCE DESCRIPTION: SEQ ID NO:145:

Phe Leu Ile Lys Gln Leu Ile Lys Leu Leu Thr Trp Leu Phe Ser Asn
 1               5                  10                  15

Cys Lys Thr Leu Leu Ser Lys Val Tyr
                20                  25

(2) INFORMATION FOR SEQ ID NO:146:

(i) SEQUENCE CHARACTERISTICS:
      (A) LENGTH: 23 amino acids
      (B) TYPE: amino acid
      (C) STRANDEDNESS: single
      (D) TOPOLOGY: linear (ii) MOLECULE TYPE: None (xi) SEQUENCE DESCRIPTION: SEQ ID NO:146:

Arg Leu Val Glu Arg Ile Arg Gln Leu Thr Ala Ser Arg Gln Leu Ile
 1               5                  10                  15

Pro Gln Leu Ile Gln Tyr Val
                20

(2) INFORMATION FOR SEQ ID NO:147:

(i) SEQUENCE CHARACTERISTICS:
      (A) LENGTH: 23 amino acids
      (B) TYPE: amino acid
      (C) STRANDEDNESS: single
      (D) TOPOLOGY: linear (ii) MOLECULE TYPE: None (xi) SEQUENCE DESCRIPTION: SEQ ID NO:147:

Arg Leu Val Arg Arg Ile Arg Gln Leu Thr Ala Ser Arg Gln Leu Ile
 1               5                  10                  15

Pro Gln Leu Ile Gln Tyr Val
                20

( 2 ) INFORMATION FOR SEQ ID NO:148:

( i ) SEQUENCE CHARACTERISTICS:
    ( A ) LENGTH: 27 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:148:

```
Leu Leu Ser Arg Val Tyr Gln Ile Leu Gln Pro Ile Leu Gln Arg Leu
 1               5                  10                  15
Ser Ala Thr Leu Gln Ala Ile Arg Glu Val Leu
            20                  25
```

( 2 ) INFORMATION FOR SEQ ID NO:149:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:149:

```
Leu Leu Ser Arg Val Tyr Gln Ile Leu Gln Pro Ile Leu Gln Arg Leu
 1               5                  10                  15
Cys Ala Thr Leu Gln Arg Ile Arg Glu Val Leu Arg
            20                  25
```

( 2 ) INFORMATION FOR SEQ ID NO:150:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:150:

```
Arg Leu Val Glu Arg Ile Arg Gln Leu Thr Ala Ser Leu Arg Gln Leu
 1               5                  10                  15
Ile Pro Gln Leu Ile Gln Tyr Val Arg Ser Leu Leu
            20                  25
```

( 2 ) INFORMATION FOR SEQ ID NO:151:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:151:

```
Leu Leu Ser Lys Val Tyr Gln Ile Leu Gln Pro Ile Leu Gln Lys Leu
 1               5                  10                  15
Ser Ala Thr Leu Gln Lys Ile Lys Glu Val Leu Lys
            20                  25
```

( 2 ) INFORMATION FOR SEQ ID NO:152:

( i ) SEQUENCE CHARACTERISTICS:
    ( A ) LENGTH: 25 amino acids (B) TYPE: amino acid
(C) STRANDEDNESS: single
(D) TOPOLOGY: linear (ii) MOLECULE TYPE: None (xi) SEQUENCE DESCRIPTION: SEQ ID NO:152:

Arg Leu Leu Thr Trp Leu Phe Ser Asn Cys Arg Thr Leu Leu Ser Arg
1               5                   10                  15
Val Tyr Gln Ile Leu Gln Pro Ile Leu
            20                  25

(2) INFORMATION FOR SEQ ID NO:153:

(i) SEQUENCE CHARACTERISTICS:
(A) LENGTH: 25 amino acids
(B) TYPE: amino acid
(C) STRANDEDNESS: single
(D) TOPOLOGY: linear (ii) MOLECULE TYPE: None (xi) SEQUENCE DESCRIPTION: SEQ ID NO:153:

Arg Leu Leu Thr Trp Leu Phe Ser Asn Arg Arg Thr Leu Leu Ser Arg
1               5                   10                  15
Val Tyr Gln Ile Leu Gln Glu Ile Leu
            20                  25

(2) INFORMATION FOR SEQ ID NO:154:

(i) SEQUENCE CHARACTERISTICS:
(A) LENGTH: 22 amino acids
(B) TYPE: amino acid
(C) STRANDEDNESS: single
(D) TOPOLOGY: linear (ii) MOLECULE TYPE: None (xi) SEQUENCE DESCRIPTION: SEQ ID NO:154:

Arg Leu Leu Thr Trp Leu Arg Arg Thr Leu Leu Ser Arg Val Tyr Gln
1               5                   10                  15
Ile Leu Gln Glu Ile Leu
            20

(2) INFORMATION FOR SEQ ID NO:155:

(i) SEQUENCE CHARACTERISTICS:
(A) LENGTH: 29 amino acids
(B) TYPE: amino acid
(C) STRANDEDNESS: single
(D) TOPOLOGY: linear (ii) MOLECULE TYPE: None (xi) SEQUENCE DESCRIPTION: SEQ ID NO:155:

Arg Ile Ala Gly Tyr Gly Leu Arg Gly Leu Ala Val Ile Ile Arg Cys
1               5                   10                  15
Ile Ile Arg Gly Leu Asn Leu Ile Phe Glu Ile Ile Arg
            20                  25

(2) INFORMATION FOR SEQ ID NO:156:

(i) SEQUENCE CHARACTERISTICS:
(A) LENGTH: 29 amino acids
(B) TYPE: amino acid
(C) STRANDEDNESS: single
(D) TOPOLOGY: linear (i i) MOLECULE TYPE: None (x i) SEQUENCE DESCRIPTION: SEQ ID NO:156:

Arg Ile Ala Gly Tyr Gly Leu Arg Gly Leu Ala Val Ile Ile Arg Ile
1               5                   10                  15
Ile Cys Arg Gly Leu Asn Leu Ile Phe Glu Ile Ile Arg
            20                  25

(2) INFORMATION FOR SEQ ID NO:157:

(i) SEQUENCE CHARACTERISTICS:
        (A) LENGTH: 30 amino acids
        (B) TYPE: amino acid
        (C) STRANDEDNESS: single
        (D) TOPOLOGY: linear (i i) MOLECULE TYPE: None (x i) SEQUENCE DESCRIPTION: SEQ ID NO:157:

Arg Ile Ala Gly Tyr Gly Leu Arg Gly Leu Ala Val Ile Pro Arg Arg
1               5                   10                  15
Ile Cys Ile Arg Gly Leu Asn Leu Ile Phe Glu Ile Ile Arg
            20                  25                  30

(2) INFORMATION FOR SEQ ID NO:158:

(i) SEQUENCE CHARACTERISTICS:
        (A) LENGTH: 29 amino acids
        (B) TYPE: amino acid
        (C) STRANDEDNESS: single
        (D) TOPOLOGY: linear (i i) MOLECULE TYPE: None (x i) SEQUENCE DESCRIPTION: SEQ ID NO:158:

Arg Ile Ile Glu Phe Ile Leu Asn Leu Gly Arg Ile Cys Ile Arg Ile
1               5                   10                  15
Ile Val Ala Leu Gly Arg Leu Gly Tyr Gly Ala Ile Arg
            20                  25

(2) INFORMATION FOR SEQ ID NO:159:

(i) SEQUENCE CHARACTERISTICS:
        (A) LENGTH: 29 amino acids
        (B) TYPE: amino acid
        (C) STRANDEDNESS: single
        (D) TOPOLOGY: linear (i i) MOLECULE TYPE: None (x i) SEQUENCE DESCRIPTION: SEQ ID NO:159:

Lys Ile Ala Gly Tyr Gly Leu Lys Gly Leu Ala Val Ile Ile Lys Ile
1               5                   10                  15
Cys Ile Lys Gly Leu Asn Leu Ile Phe Glu Ile Ile Lys
            20                  25

(2) INFORMATION FOR SEQ ID NO:160:

(i) SEQUENCE CHARACTERISTICS:
        (A) LENGTH: 28 amino acids
        (B) TYPE: amino acid
        (C) STRANDEDNESS: single
        (D) TOPOLOGY: linear (i i) MOLECULE TYPE: None (x i) SEQUENCE DESCRIPTION: SEQ ID NO:160:

Arg Val Ile Arg Val Val Gln Gly Ala Cys Arg Ala Ile Arg His Ile
1               5                   10                  15

Pro Arg Arg Ile Arg Gln Gly Leu Arg Arg Ile Leu
            20              25

( 2 ) INFORMATION FOR SEQ ID NO:161:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:161:

Arg Val Ile Glu Val Val Gln Gly Ala Cys Arg Ala Ile Glu His Ile
1               5                   10                  15

Pro Arg Arg Ile Glu Gln Gly Leu Glu Arg Ile Leu
            20              25

( 2 ) INFORMATION FOR SEQ ID NO:162:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:162:

Arg Val Ile Glu Val Val Gln Gly Ala Cys Arg Ala Ile Glu His Ile
1               5                   10                  15

Pro Arg Arg Ile Arg Gln Gly Leu Glu Arg Ile Leu
            20              25

( 2 ) INFORMATION FOR SEQ ID NO:163:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:163:

Arg Val Ile Glu Val Val Gln Gly Ala Cys Arg Ala Ile Arg His Ile
1               5                   10                  15

Pro Arg Arg Ile Glu Gln Gly Leu Glu Arg Ile Leu
            20              25

( 2 ) INFORMATION FOR SEQ ID NO:164:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:164:

Arg Val Ile Glu Val Val Gln Gly Ala Cys Arg Ala Ser Arg His Ile
1               5                   10                  15

Pro Arg Arg Ile Arg Gln Gly Leu Glu Arg Ile Leu 20        25

(2) INFORMATION FOR SEQ ID NO:165:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:165:

Arg Val Ile Glu Val Val Gln Gly Ala Cys Arg Ala Ile Arg His Ile
1               5                   10                  15
Pro Arg Arg Ser Arg Gln Gly Leu Glu Arg Ile Leu
            20                  25

(2) INFORMATION FOR SEQ ID NO:166:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:166:

Phe Leu Ile Arg Gln Leu Ile Glu Leu Leu Thr Trp Leu Phe Ser Asn
1               5                   10                  15
Cys Arg Thr Leu Leu Ser Glu Val Tyr
            20                  25

(2) INFORMATION FOR SEQ ID NO:167:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:167:

Leu Leu Ser Glu Val Tyr Gln Ile Leu Gln Pro Ile Leu Gln Glu Leu
1               5                   10                  15
Ser Ala Thr Leu Gln Arg Ile Arg Glu Val Leu Arg
            20                  25

(2) INFORMATION FOR SEQ ID NO:168:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:168:

Tyr His Glu Leu Arg Asp Leu Leu Leu Ile Val Thr Arg Ile Val Glu
1               5                   10                  15
Leu Leu Gly Arg Glu
            20

(2) INFORMATION FOR SEQ ID NO:169:

(i) SEQUENCE CHARACTERISTICS:
    (A) LENGTH: 28 amino acids
    (B) TYPE: amino acid
    (C) STRANDEDNESS: single
    (D) TOPOLOGY: linear (ii) MOLECULE TYPE: None (xi) SEQUENCE DESCRIPTION: SEQ ID NO:169:

```
Arg Val Ile Glu Val Val Gln Gly Ala Tyr Arg Ala Ile Arg His Ile
 1               5                  10                      15
Pro Arg Arg Ile Arg Gln Gly Leu Glu Arg Ile Leu
                20                  25
```

ANTIMICROBIAL PEPTIDES

This invention was made with funding from the U.S. government, which has certain rights therein.

The present application is a regular patent application based on provisional patent application Ser. No. 60/010,634 filed on Jan. 26, 1996.

BACKGROUND OF THE INVENTION

The development of antimicrobial agents led to a significant decrease in morbidity and mortality from infectious disease in this century. This accomplishment was largely due to the widespread use of the major classes of antibiotics, such as the sulfonamides, penicillins, cephalosporins, aminoglycosides, tetracyclines (Goodman et al., *The Pharmacological Basis of Therapeutics*, Macmillan Publishing, New York, 1985). However, in recent years, the trend in reducing infectious disease mortality has been threatened by the emergence of resistant strains of microorganisms that are no longer susceptible to the currently available antimicrobial agents. As a result, maintenance of public health requires that new antimicrobial agents be developed to counter these emerging resistant strains in order that diseases previously considered to be under control do not reemerge.

Recently, a group of peptides with antimicrobial properties has drawn attention as potential therapeutic agents. Such peptides include the magainins produced by amphibians and the cecropins produced by insects (Jacob et al., Ciba Foundation Symposium, John Wiley & Sons, New York, 1994). These peptides are believed to function as multimeric structures that insert into biological membranes to form pores that disrupt membrane structure and cause a loss of osmotic integrity. Although a wide sequence variation has been observed among these peptides, they all appear to retain a characteristic positively charged amphipathic helical structure, indicating that structural organization is a critical determinant of their membrane-disruptive functionality.

The magainins have been extensively investigated for clinical application, and have been found to be effective in treating systemic *E. coli* infections in a mouse model. Trials are underway to evaluate a magainin analog for effectiveness as a topical antimicrobial for the treatment of impetigo (Jacob et al., Antimicrobial Peptides, Ciba Foundation Symposium, 197–223, 1994).

Intensive investigation into the cytopathology caused by the human immunodeficiency virus (HIV) has included the structural analysis of its proteins. The HIV transmembrane (TM) protein (gp41), which is incorporated into the membrane of the virion, comprises three domains: an ectodomain, a transmembrane region and an intravirion endomain region, the latter comprising approximately 150 amino acids. The endodomain contains two regions in its carboxy terminus which have a high hydrophobic moment and are capable of forming amphipathic α-helices (Eisenberg et al., Biopolymers 29: 171–177, 1990). This structural feature of the endodomain is similar to the three-dimensional structure of known cytolytic peptides, despite the lack of any amino acid sequence homology with them.

Miller et al. demonstrated that synthetic peptides corresponding to sequences found in the carboxy terminus of the TM protein of both HIV-1 and simian immunodeficiency virus (SIV), termed HIV-L and SIV-L, respectively, were capable of cytolytic activity against procaryotic and mammalian cells (Miller et al., AIDS Res. and Hum. Retro. 7: 511–519, 1991). The term "LLP" was used to designate lytic peptides derived from lentiviruses (such as HIV and SIV). Other studies confirmed the antimicrobial activity of these peptides (Srinivas et al., J. Biol. Chem. 267: 7121–7127, 1992; Arroyo et al., J. Virol. 69: 4095–4102, 1995). Antifungal activity has also been demonstrated for a synthetic peptide corresponding to this region (Zhong et al., Int. J. Peptide Protein Res. 45: 337–347, 1995). In contrast to other antimicrobial peptides which are specifically encoded by their own genes, LLPs are unique in that they are derived from naturally occurring sequences that are part of a larger folded protein.

Further analysis confirmed that LLPs could cause membrane perturbation in mammalian cells (Srinivas et al., J. Biol. Chem. 267: 7121–7127, 1992; Miller et al., Virology 196: 89–100, 1993), Sf9 cells (Chernomordik et al., J. Virol. 68: 7115–7123, 1994) and *E. coli* (Arroyo et al., J. Virol. 69: 4095–4102, 1995). Other studies demonstrated that synthetic peptides corresponding to a portion of the HIV TM protein also could inhibit the fusion of HIV-infected CD4+ cells (Srinivas et al., J. Biol. Chem. 267: 7121–7127, 1992). Moreover, a similar synthetic peptide corresponding to the same region of gp41 directly interacted with the lipid bilayer of microsomal membranes (Gawrisch et al., Biochemistry 38: 3112–3118, 1993) and caused pore formation in membranes (Chernomordik et al., J. Virol. 68: 7115–7123, 1994).

In further studies designed to analyze the mechanism of HIV cytopathogenesis, synthetic peptides corresponding to regions of the HIV TM protein were shown to bind to calmodulin (CAM), a critical mediator of Ca2+-based signal transduction in eucaryotic cells (Miller et al., AIDS Res. and Hum. Retro. 9: 1057–1066, 1993; Srinivas et al., J. Biol. Chem. 268: 22895–22899, 1993). An analogous peptide from SIV was also shown to bind CaM (Yuan et al., Biochemistry 34: 10690–10696, 1995). These findings imply that HIV and other lentiviruses may interfere with the cellular signalling pathways by sequestering CaM through a TM protein-mediated mechanism.

Certain analogs of LLP1 have been tested for activity in erythrocyte lysis assays and CaM binding assays (Tencza et al., J. Virol. 69: 5199–5202, 1995). For example, analogs with a single amino acid replacement that produced a charge substitution, e.g., Arg→Glu, showed significantly decreased cytolytic potential and CaM binding ability. Analogs in which a hydrophobic residue was replaced by a non-hydrophobic amino acid, e.g., Ile→Ser, exhibited a significant reduction in cytolytic activity, but less reduction in the ability to bind CaM.

Analysis of gp41 from diverse HIV isolates from which LLP1 has been obtained reveals a 28-amino acid segment which exhibits a conservation of charge number and amphipathic potential, even though amino acid sequence variation exists in this region of gp41 from different virus isolates (Miller et al., Virology 196: 89–100, 1993).

Examination of sequences from a variety of lentiviruses also revealed an LLP1 region in SIV and equine infectious anemia virus (EIAV) (Miller et al., AIDS Res. Hum. Retroviruses 7: 511–519, 1991).

Another sequence motif was identified in the HIV-1 TM protein upstream of the LLP1 sequence (Eisenberg et al., Biopolymers 29: 171–177, 1990), and was designated LLP2. Similar sequences existing in the SIV TM protein have also been identified. The SIV protein contains an unusually long LLP2 region (amino acids 771–817 of SIV MM239). The LLP2 sequences among HIV-1 isolates are well conserved, having much less amino acid variation than seen in LLP1 sequences (Myers et al., Human Retroviruses and AIDS 1995, Los Alamos National Laboratory, 1995).

SUMMARY OF THE INVENTION

The invention is directed to antimicrobial peptides which correspond in sequence to selective amino acid sequences in viral transmembrane proteins. In particular, the proteins are derived from lentiviruses, primarily HIV and SIV. The peptides comprise arginine-rich sequences, which, when modeled for secondary structure, display a high amphipathicity and hydrophobic moment. They are highly inhibitory to microorganisms, while being significantly less active in regard to mammalian cells. As a result, the peptides of the invention may be defined as selective antimicrobial agents. The invention is also directed to antimicrobial peptides which are structural and functional analogs and homologs of the peptides and which exhibit selective inhibitory activity towards microorganisms. The invention is also directed to pharmaceutical compositions comprising the antimicrobial peptides of the invention and to methods for their use in inhibiting microbial growth and treatment of microbial infections.

BRIEF DESCRIPTION OF THE DRAWINGS

The present invention may be better understood with reference to the attached drawings of which FIG. 1. shows growth inhibition of *Staphylococcus aureus* (SA) and methicillin-resistant *Staphylococcus aureus* (MRSA) by peptides LLP1 and magainin 2.

DETAILED DESCRIPTION

Figure 1:
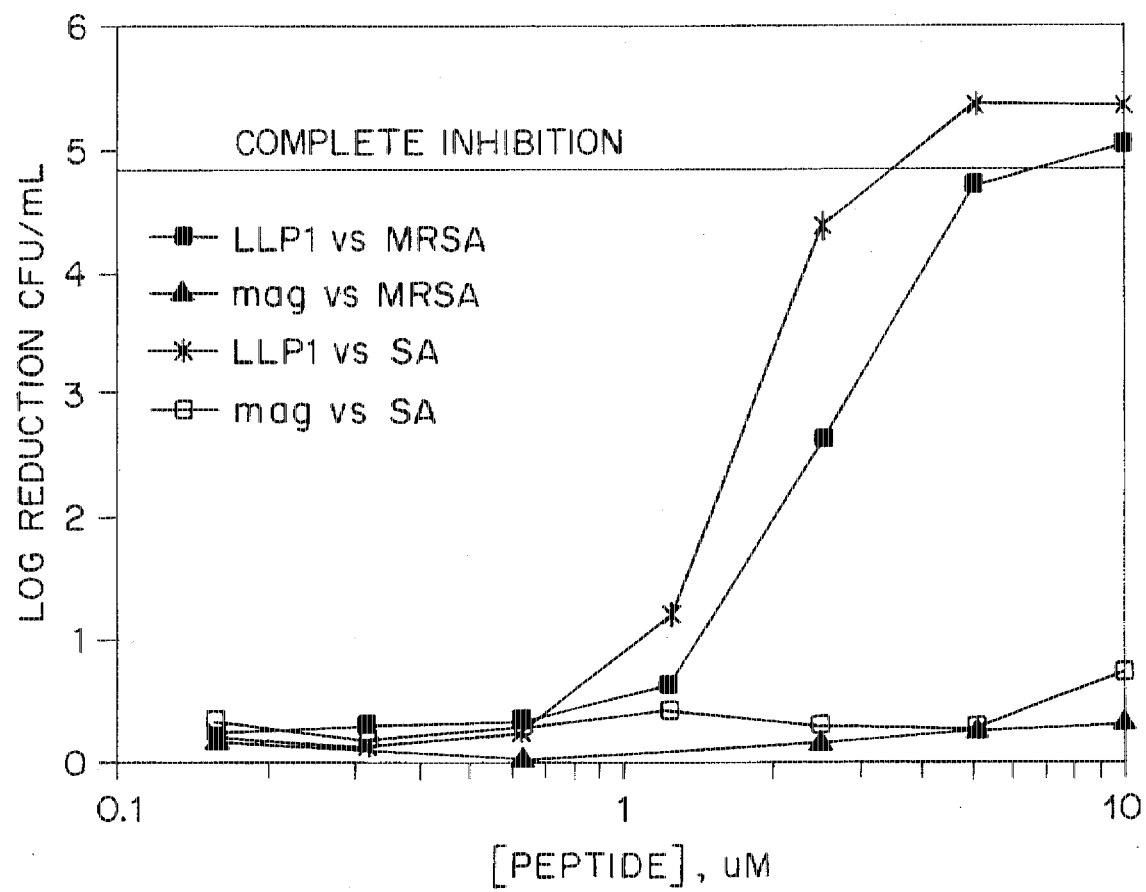

The antimicrobial peptides of the present invention are peptides which exhibit antimicrobial activity against diverse microorganisms. In one aspect of the invention, the peptides correspond to amino acid sequences in the TM proteins of lentiviruses, in particular, HIV and SIV. These peptides comprise arginine-rich sequences, which, when modeled for secondary structure, display high amphipathicity and hydrophobic moment. The antimicrobial peptides are highly inhibitory to microorganisms but significantly less toxic to red blood cells and other normal mammalian cells. As a result, these peptides can be characterized as selective antimicrobial agents.

As used herein, the term "antimicrobial" refers to the ability of the peptides of the invention to prevent, inhibit or destroy the growth of microbes such as bacteria, fungi, protozoa and viruses.

As used herein, the term "peptide" refers to an oligomer of at least two contiguous amino acids, linked together by a peptide bond.

In another embodiment of the invention, the antimicrobial peptides are structural and functional analogs of the naturally occurring parent peptides which exhibit selective toxicity for microorganisms.

As used herein, the term "analog" refers to a peptide which contains substitutions, rearrangements, deletions, additions and/or chemical modifications in the amino acid sequence of parent peptide, and retains the structural and functional properties of the parent peptide.

In another embodiment of the invention, the antimicrobial peptides are structural and functional homologs of the naturally occurring parent peptides which exhibit selective toxicity for microorganisms.

As used herein, the term "homolog" refers to a peptide, the sequence of which is at least 80% homologous to the amino acid sequence of a parent peptide, and retains the structural and functional properties of the parent peptide.

The amino acid sequences of the antimicrobial peptides of the invention correspond to or are analogous to or homologous to peptides LLP1 and LLP2, which, in turn, correspond to residues 828-855 and 768-788 of the HIV-1 TM protein (gp41) (strain HXB2R), respectively; peptides SLP-1, SLP-2A and SLP-2B (SLP2 region), which, in turn, correspond to residues 852-879, 771-795 and 790-817 of the SIV TM protein (MM239 strain of SIV), respectively; and peptide ELP, which corresponds to residues 808-836 of EIAV (Wyoming strain). The striking feature of these sequences is their lack of sequence homology to known cytolytic peptides (e.g. magainins); however, each is rich in positively charged residues and is predicted to form an amphipathic helix. This structure imparts to each of the peptides a unique but potent antimicrobial activity.

Numbering of residues in the naturally occurring HIV and SIV LLP sequences is according to Myers, Human Retroviruses and AIDS Database, Los Alamos National Laboratory, New Mexico. The specific strains used to derive these peptides were HIV-HXB2R and SIVMM239. The sequence of the EIAV peptide is found in Rushlow et al., Virology 155: 309-321, 1986.

The antimicrobial peptides of the invention are unique in their functional properties. In general, cytolytic peptides can be classified into two major functional types. Antibacterial peptides (magainins and cecropins, for example) specifically kill bacteria. Hemolytic peptides, on the other hand, generally both kill bacteria and lyse red blood cells; melittin from bee venom is an example of such a peptide. The antimicrobial peptides of the present invention are moderately hemolytic; they do lyse red blood cells, but only at high concentrations. This is in contrast to melittin, which is highly active against red blood cells and shows little selectivity (Habermann, E., Science 177: 314-322, 1972). The unique structure of the antimicrobial peptides of the invention imparts high potency while maintaining selectivity. The potency of the antimicrobial peptides compares very favorably to that of magainin. LLP1 rapidly kills both Gram-positive and Gram-negative bacteria, demonstrating a broad spectrum of activity. The antimicrobial peptides of the invention exhibit activity against *S. aureus*, methicillin-resistant *S. aureus*, *Pseudomonas aeruginosa* (*P. aeruginosa*), *Enterococcus faecalis* (*E. faecalis*), vancomycin-resistant *E. faecalis*, and *S. marcescens*, among others.

The structural properties defining the antimicrobial peptides of the invention include, inter alia, a significant number of positively charged amino acid residues and the ability to form three-dimensional amphipathic helical structures (Eisenberg et al., Biopolymers 29: 171-177, 1990). Functional properties include, inter alia, a selective antimicrobial cytolytic activity, but minimal cytolytic activity toward mammalian cells.

The structural formulae of the antimicrobial peptides of the invention corresponding to regions of TM proteins derived from HIV-1, SIV, and EIAV are listed in TABLE 1.

TABLE 1

Parent Antimicrobial Peptides

| Peptide Name | Amino Acid Sequence | Sequence Source[1] |
|---|---|---|
| LLP1 (SEQ ID NO: 1) | RVIEVVQGACRAIRHIPRRIRQGLERIL | HIVHXB2R 828–855 |
| LLP2 (SEQ ID NO: 2) | YHRLRDLLLIVTRIVELLGRR | HIVHXB2R 768–788 |
| SLP1 (SEQ ID NO: 3) | DLWETLRRGGRWILAIPRRIRQGLELTL | SIVMM239 852–879 |
| SLP2A (SEQ ID NO: 4) | FLIRQLIRLLTWLFSNCRTLLSRVY | SIVMM239 771–795 |
| SLP2B (SEQ ID NO: 5) | LLSRVYQILQPILQRLSATLQRIREVLR | SIVMM239 790–817 |
| ELP (SEQ ID NO: 6) | RIAGYGLRGLAVIIRICIRGLNLIFEIIR | EIAV 808–836 | wherein:
A = Ala = Alanine
R = Arg = Arginine
N = Asn = Asparagine
D = Asp = Aspartic acid
B = Asx = Asparagine or aspartic acid
C = Cys = Cysteine
Q = Gln = Glutamine
E = Glu = Glutamic acid
Z = Glx = Glutamine or glutamic acid
G = Gly = Glycine
H = His = Histidine
I = Ile = Isoleucine
L = Leu = Leucine
K = Lys = Lysine
M = Met = Methionine
F = Phe = Phenylalanine
P = Pro = Proline
S = Ser = Serine
T = Thr = Threonine
W = Trp = Tryptophan
Y = Tyr = Tyrosine
V = Val = Valine

[1] Sequences of the family of LLPs derived from HIV and SIV envelope proteins are consistent with the numbering in Myers. The sequence of ELP, the peptide derived from the ENV protein of EIAV, is from the Wyoming strain (Rushlow et al., 1986).

A peptide analog or homolog within the scope of the present invention may be identified by the following criteria: (1) the parent peptide of the analog is an antimicrobial peptide having a sequence which corresponds to a viral TM protein, particularly a lentivirus TM protein; (2) the amino acid sequence of the peptide is capable of forming an amphipathic helix and contains a number of positively charged residues; (3) the peptide is selectively antimicrobial in its biological function and has minimal cytolytic activity toward mammalian cells.

In the design of the peptide analogs of the antimicrobial peptides of the invention, the allowed amino acid interchanges which are contemplated include, inter alia, the substitution of an individual residue in the peptide with a residue that falls within the same chemical subset, e.g., a hydrophobic amino acid replaced by the same or a positively charged residue with the same. This degree of substitution allows for the construction of peptide analogs from the parent structure which retain the structural and functional properties of the parent peptide, without undue experimentation.

Analogs may also contain non-conservative amino acid interchanges provided that structural and functional properties are retained or enhanced. A singular characteristic of the antimicrobial peptides of the present invention is the presence of a significant number of positively charged residues, especially arginine. Analogs and homologs within the scope of the invention include those that encompass substitutions which retain the overall charge characteristics of the peptides. Preferably, the peptides of the invention have a net charge of at least +3 at neutral pH. Net charge is calculated by adding the sum of the charge value of positively charged amino acids (arginine, lysine, histidine) (+1) and the charge value of the negatively charged amino acids (aspartic acid, glutamic acid) (-1). Thus, the positively-charged arginines in the peptides may be substituted by histidine or lysine so as to retain positively charged residues. Analogs may be designed which increase the number of positively charged amino acids so long as the antimicrobial activity of the peptide is not diminished, for example, the number of arginine residues may be increased. An analog which increased the number of positive charges in an LLP1 analog peptide has been shown to be more toxic to bacteria than the parent LLP1 (Miller et al., Virology 196: 89–100, 1993); (Table 7, infra).

Additional analogs of the peptides within the scope of the present invention can have an altered number of hydrophobic amino acids based on the parent peptide, producing peptides having altered specificity. For example, an increase in hydrophilic residues appears to reduce antimicrobial effectiveness. However, such changes appear to increase antimicrobial specificity by reducing undesired hemolytic activity. Therefore, based on the teachings and guidance herein, one skilled in the art can design analogs within the scope of the invention which have a desired potency and selectivity.

In the design of peptide homologs of the antimicrobial peptides of the invention, the amino acid changes which are contemplated include, inter alia, the replacement of amino acid residues in a parent peptide such that the homologous peptide retains the structural and functional properties of the parent peptide.

A primary common and recognizable feature of the antimicrobial peptides of the present invention is their secondary structure, or more specifically, their potential to form amphipathic structures, which may be in the form of an α-helix or a β conformation. An α-helix motif, for example, comprises residues arranged such that 3.5 amino acid residues complete 1 turn of the helix. An estimate of amphipathicity may therefore be made by examination of the amino acid sequence; for example, peptides comprising amino acid residues arranged in a hydrophobic-hydrophobic-hydrophilic-hydrophilic repeating motif are highly likely to form an α-helix. Amino acid residues arranged to alternate in a hydrophobic-hydrophilic-hydrophobic-hydrophilic repeating motif are likely to form a β conformation. Such "ideal" motifs are found in the antimicrobial peptides of the invention and as such may be used by those skilled in the art as a foundation for engineering additional amphipathic peptide analogs of the invention without great difficulty based on the teachings herein. The antimicrobial peptides of the invention may further contain proline or glycine, amino acid residues which can be tolerated within a general amphipathic structure and may indicate demarcations between different amphipathic regions. These residues may impart a structure which enhances the activity and selectivity of a peptide because of a bend or kink between helices. For example, a solidly helical structure may be less selective (e.g. LLP2, SLP2A). Homologs may also be engineered, using these structural considerations, that are at least 80% homologous to the amino acid sequence of a parent peptide, and retain the structural and essential antimicrobial functional properties of the parent peptide.

Analogs and homologs in which the amphipathicity of a peptide is increased by additions, deletions and/or substitutions of amino acids in a parent peptide are within the scope of the invention.

Analogs and/or homologs of the invention preferably contain at least one cysteine which, by virtue of its capacity to form a disulfide bond, can confer high potency and a very high degree of bactericidal activity to a peptide containing such a residue. A peptide preferably contains a single cysteine residue to ensure that any disulfide bond formed by the cysteine would be intermolecular and result in a disulfide-linked dimeric peptide (e.g. bis-LLP1). The residue to be replaced by cysteine is preferably neither very hydrophobic nor basic and lies on the interface of the hydrophilic and hydrophobic faces of the amphipathic structure when modeled as such. Computer modeling programs such as "Helicalwheel" may be used to design such peptides (Genetics Computer Group, Madison, Wis.).

The antimicrobial peptides of the invention generally comprise a positively charged C-terminus. However, those peptides having this characteristic generally have some hemolytic activity, and analogs which optimize antimicrobial selectivity (i.e., decrease hemolytic activity) may be those which replace the positively charged C-terminus with negatively charged or hydrophobic residues (Merrifield et al., Antimicrobial Peptides, Ciba Foundation Symposium, Wiley, Chichester, 5–26, 1994). Since reduction of the basic character of the C-terminus may provide antimicrobial selectivity, analogs are provided in which the amino acids of the C-terminus region may be reversed in situ, or, alternatively, the N-terminus and C-terminus regions may be interchanged. The peptide is then comprised of a positively charged N-terminus and a hydrophobic C-terminus.

Analogs and homologs which are chimeras of particular antimicrobial peptides and/or other cytolytic peptides are within the scope of the present invention, provided that the structural and functional properties described herein are retained.

In another embodiment of the invention, the use of D-amino acids in place of L-amino acids in the peptides may provide increased metabolic stability, since peptides containing D-amino acids are resistant to mammalian proteases, which generally cleave peptides composed of L-amino acids. For example, cecropin analogs containing D-amino acids exhibit antibacterial activity (Merrifield et al., Antimicrobial Peptides, Ciba Foundation Symposium, Wiley, Chichester, 5–26, 1994).

In addition, peptide analogs and homologs of the invention containing reduced leucine stretches, such as those present in LLP2 derived sequences, may also be more stable, microbially active and easier to synthesize. In designing peptides with positively charged residues, lysine may be used to minimize cost.

The present invention is also directed to peptide analogs and homologs which are truncated, i.e., shorter than the parent amino acid sequence or to truncated parent peptide fragments. A minimal length required to effectuate ion-channel formation in membranes is believed to be a peptide of 8–12 amino acid residues in length. It has been suggested that the antimicrobial peptides may dimerize so as to comprise the approximately 20 amino acid length believed to be required to transverse a membrane (Zhong et al., Int. J. Peptide Protein Res. 45: 337–347, 1995). As discussed above, the inclusion of a cysteine residue in an antimicrobial peptide is of importance in facilitating the formation of intramolecular or intermolecular disulfide bonds which can stabilize a dimeric peptide. A 21-amino acid segment of LLP1 was capable of pore formation in planar lipid bilayers in vitro, although it was not tested for antimicrobial activity (Chernomordik et al., J. Virol. 68: 7115–7123, 1994). The design of analogs of minimal length can optimize potency of the peptides in terms of effectiveness per mass.

The invention is further directed to peptides having a primary structure selected from the group consisting of:

a) $R^1-R^2-R^2-R^3-R^2-R^2-R^3-R^3-R^2-C-R^1-R^2-R^2-R^1-R^1-R^2-P-R^1-R^1-R^2-R^1-R^3-R^2-R^2-R^3-R^1-R^2-R^2$;

b) $R^2-R^2-R^3-R^3-R^2-R^1-R^1-R^3-R^3-R^1-R^2-R^2-R^2-R^2-R^2-P-R^1-R^1-R^2-R^1-R^3-R^3-R^2-R^3-R^2-R^3-R^2$;

c) $R^2-R^2-R^3-R^3-R^2-R^1-R^1-R^3-C-R^1-R^2-R^2-R^2-R^2-R^2-P-R^1-R^1-R^2-R^1-R^3-R^3-R^2-R^3-R^2-R^3-R^2$;

d) $R^2-R^1-R^1-R^2-R^1-R^3-R^2-R^2-R^2-R^2-P-R^3-R^1-R^2-R^2-R^3-R^2-R^2-R^3-R^1-R^1$;

e) $R^2-R^2-R^2-R^1-R^3-R^2-R^2-R^3-R^2-R^2-R^3-R^2-R^2-R^2-R^3-R^3-C-R^1-R^3-R^2-R^2-R^3-R^1-R^2-R^2$;

f) $R^2-R^2-R^2-R^1-R^3-R^2-R^2-R^3-R^2-R^2-R^3-R^2-R^2-R^2-P-R^3-R^3-C-R-R^1-R^3-R^2-R^2-R^3-R^1-R^2-R^2$;

g) $R^2-R^2-R^3-R^1-R^2-R^2-R^3-R^2-R^2-R^3-P-R^2-R^2-R^3-R^1-R^2-R^3-R^2-R^3-R^2-R^3-R^1-R^2-R^1-R^3-R^2-R^2-R^1$;

h) $R^1-R^2-R^2-R^3-R^2-R^3-R^2-R^1-R^3-R^2-R^2-R^2-R^2-P-R^1-R^2-C-R^2-R^1-R^3-R^2-R^3-R^2-R^2-R^2-R^3-R^2-R^2-R^1$;

i) $R^1-R^2-R^2-R^3-R^2-R^2-R^3-R^3-R^2-C-R^1-R^2-R^2-R^1-R^1-R^2-P-R^1-R^1-R^2-R^1$;

j) $R^2-R^2-R^3-R^3-R^2-C-R^1-R^2-R^2-R^1-R^1-R^2-P-R^1-R^1-R^2-R^1$;

k) $R^3-R^2-C-R^1-R^2-R^2-R^1-R^1-R^2-P-R^1-R^1-R^2-R^1$;

wherein
$R^1$ is a basic amino acid selected from the group consisting of arginine, lysine, and histidine;

$R^2$ is a hydrophobic amino acid selected from the group consisting of tyrosine, isoleucine, leucine, valine, alanine, phenylalanine, tryptophan and methionine;

$R^3$ is an amino acid selected from the group consisting of serine, threonine, glutamine, asparagine, aspartic acid, glutamic acid, and glycine;

C is the amino acid cysteine and P is the amino acid proline.

The following analogs and homologs, derived from the parent peptides shown in TABLE 1, are also exemplary of the peptides of the present invention, and have the following primary structural formulae:

LLP1 ANALOGS:

RVIEVVQGACRAIRHIPRRIR (SEQ ID NO:7)
RVIRVVQGACRAIRHIPRRIR (SEQ ID NO:10)
RVIEVVRGACRAIRHIPRRIR (SEQ ID NO:11)
RVIEVVQGICRAIRHIPRRIR (SEQ ID NO:12)
RVISVVQGACRAIRRIPRRIR (SEQ ID NO:13)
RVIRVVQGACRAIRHIPRRIRQGLERIL (SEQ ID NO:14)
RVIEVVRGACRAIRHIPRRIRQGLERIL (SEQ ID NO:15)
RVIEVVQGICRAIRHIPRRIRQGLERIL (SEQ ID NO:16)
RVISVVQGACRAIRRIPRRIRQGLERIL (SEQ ID NO:17)
RVIEVVQGACRAIRHIPRRIRQILERIL (SEQ ID NO:18)
RVIEVVQGACRAIRHIPRRIRQGLRRIL (SEQ ID NO:19)
RVIRVVQGACRAIRHIPRRIR (SEQ ID NO:20)
RVIEVVRGACRAIRHIPRRIR (SEQ ID NO:21)
RVIEVVQGICRAIRHIPRRIR (SEQ ID NO:22)
RVIEVVQGACRAIRRIPRRIR (SEQ ID NO:23)
RVIRVVQGACRAIRHIPRRIRQGLERIL (SEQ ID NO:24)
RVIEVVRGACRAIRHIPRRIRQGLERIL (SEQ ID NO:25)
RVIEVVQGICRAIRHIPRRIRQGLERIL (SEQ ID NO:26)
RVIEVVQGACRAIRRIPRRIRQGLERIL (SEQ ID NO:27)
VVRGACRAIRHIPRRIR (SEQ ID NO:28)
VVQGICRAIRHIPRRIR (SEQ ID NO:29)
VVQRACRAIRRIPRRIR (SEQ ID NO:30)
VVRGACRAIRHIPRRIRGLERIL (SEQ ID NO:31)
VVQGICRAIRHIPRRIRGLERIL (SEQ ID NO:32)
VVQGACRAIRRIPRRIRGLERIL (SEQ ID NO:33)
GACRAIRRIPRRIR (SEQ ID NO:34)
GACRAIRRIPRRIRGLERIL (SEQ ID NO:35)
VVQRACRAIRHIPRRIR (SEQ ID NO:36)
RACRAIRHIPRRIR (SEQ ID NO:37)
RVIRVVRGACRAIRHIPRRIR (SEQ ID NO:38)
RVIRVVRGACRAIRHIPRRIR (SEQ ID NO:39)
RRIRHIPRAIRVVQGAC (SEQ ID NO:40)
RIRRPIHRIARCAGQVVEIVR (SEQ ID NO:41)
LIRELGQRIRRPIHRIARCAGQVVEIVR (SEQ ID NO:42)
LIRELGQRIRRPIHRIARCAGQVVRIVR (SEQ ID NO:43)
LIRELGQRIRRPIHRIARCAGRVVEIVR (SEQ ID NO:44)
LIRELGQRIRRPIHRIARCIGQVVEIVR (SEQ ID NO:45)
LIRELGQRIRRPIRRIARCAGQVVEIVR (SEQ ID NO:46)
LIRELGIRIRRPIHRIARCAGQVVEIVR (SEQ ID NO:47)
LIRRLGQRIRRPIHRIARCAGQVVEIVR (SEQ ID NO:48)
RIRRPIHRIARCAGQVVEIVR (SEQ ID NO:49)
RIRRPIHRIARCAGQVVRIVR (SEQ ID NO:50)
RIRRPIHRIARCAGRVVEIVR (SEQ ID NO:51)
RIRRPIHRIARCIGQVVEIVR (SEQ ID NO:52)
RIRRPIRRIARCAGQVVEIVR (SEQ ID NO:53)
RIRRPIHRIIRCIGQVVRIVR (SEQ ID NO:54)
RIRRPIRRIIRCIGQVVEIVR (SEQ ID NO:55)
LIRELGQRIRRPIHRIARCAGQVV (SEQ ID NO:56)
LIRELRQRIRRPIHRIARCARQVV (SEQ ID NO:57)
LIRELGQRIRRPIHRIARCAGRVV (SEQ ID NO:58)
LIRELGQRIRRPIHRIARCIGQVV (SEQ ID NO:59)
LIRELGQRIRRPIRRIARCAGQVV (SEQ ID NO:60)
LIRELGIRIRRPIHRIARCAGQVV (SEQ ID NO:61)
LIRRLGQRIRRPIHRIARCAGQVV (SEQ ID NO:62)
LIRELGQRIRRPIHRIARCAG (SEQ ID NO:63)
LIRELGQRIRRPIHRIARCAR (SEQ ID NO:64)
LIRELGQRIRRPIHRIARCAI (SEQ ID NO:65)
LIRELGQRIRRPIHRIARCIG (SEQ ID NO:66)
LIRELGQRIRRPIRRIARCAG (SEQ ID NO:67)
LIRELGIRIRRPIHRIARCAG (SEQ ID NO:68)
LIRRLGQRIRRPIHRIARCAG (SEQ ID NO:69)
RAIRRAIRGAPRAIL (SEQ ID NO:70)
RAIRRAIRGAPRAILRAIL (SEQ ID NO:71)
KVIEVVQGACKAIKHIPKKIKQGLEKIL (SEQ ID NO:72)

SLP-1 ANALOGS:

LWETLRRGGRWILAIPRRIR (SEQ ID NO:73)
DLWETLRRIIRWILAIPRRIRQGLELTL (SEQ ID NO:74)
DLWETLRRGGRWILAIPRRIRQGLELCL (SEQ ID NO:75)
DLWETLRRGCRWILAIPRRIRQGLELTL (SEQ ID NO:76)
DLWETLRRIIRWILAIPRRIRQGLELCL (SEQ ID NO:77)
LWETLRRGGRWILAIPRRIRQGLELTL (SEQ ID NO:78)
LWETLRRGGRWILAIPRRIRQGLELCL (SEQ ID NO:79)
LWETLRRGCRWILAIPRRIRQGLELTL (SEQ ID NO:80)
LWRTLRRGGRWILAIPRRIRQGLELTL (SEQ ID NO:81)
LWETLRRGGRWILAIPRRIRQGLRLTL (SEQ ID NO:82)
LWETLRRGGRWILAIPRRIRRGLELTL (SEQ ID NO:83)
LWETLRRGGRWILAIPRRIRRQIELTL (SEQ ID NO:84)
LWELLRRGGRWILAIPRRIRQGLELTL (SEQ ID NO:85)
LWRLLRRGGRWILAIPRRIRQGLELTL (SEQ ID NO:86)
DLWETLRRIIRWILAIPRRIR (SEQ ID NO:87)
DLWETLRRGGRWILAIPRRIR (SEQ ID NO:88)
DLWETLRRGCRWILAIPRRIR (SEQ ID NO:89)
LWETLRRGGRWILAIPRRIR (SEQ ID NO:90)
LWETLRRIIRWILAIPRRIR (SEQ ID NO:91)
LWETLRRGCRWILAIPRRIR (SEQ ID NO:92)
LWETLRRGGRWILAIPRRIR (SEQ ID NO:93)
LWETLRRGCRWILAIPRRIR (SEQ ID NO:94)
LWETLRRIIRWILAIPRRIR (SEQ ID NO:95)
LWELLRRGGRWILAIPRRIR (SEQ ID NO:96)
LWRLLRRGGRWILAIPRRIR (SEQ ID NO:97)
LRRGGRWILAIPRRIR (SEQ ID NO:98)
LWETLRRGGRWILAIPRAIL (SEQ ID NO:99)
LRRGGRWILAIPRAIL (SEQ ID NO:100)
LWETLRRGGRWILAIPREIL (SEQ ID NO:101)
LRRGGRWILAIPREIL (SEQ ID NO:102)
WILAIPRRIRGGRLWETL (SEQ ID NO:103)
WETLPRRIRGGRLWILAI (SEQ ID NO:104)
RIRRPIALIWRGGRRLTEWL (SEQ ID NO:105)
DLWETLKKGGRWILAIPRRIKQGLELTL (SEQ ID NO:106)
LWETLGRVGRWVLAIPRRIRQGLELAL (SEQ ID NO:107)

LLP2 ANALOGS:

YHRLRRLLLIVTRIVELLGRR (SEQ ID NO:108)
YHRLRDLLRIVTRIVELLGRR (SEQ ID NO:109)
YHRLRDLLLIVRRIVELLGRR (SEQ ID NO:110)
YHRLRDLLLIVTRIVRLLGRR (SEQ ID NO:111)
YHRLRDLLLIVTRIVCLLGRR (SEQ ID NO:112)
YHRLRDLLLIVRRIVCLLGRR (SEQ ID NO:113)
YHRLLRDLLIVTRIVELLGRR (SEQ ID NO:114)
YHRLRRLLLIVTRIVELL (SEQ ID NO:115)
YHRLRDLLRIVTRIVELL (SEQ ID NO:116)
YHRLRDLLLIVRRIVELL (SEQ ID NO:117)

YHRLRDLLLIVTRIVRLL (SEQ ID NO:118)
YHRLRDLLLIVTRIVCLL (SEQ ID NO:119)
YHRLRDLLLIVRRIVCLL (SEQ ID NO:120)
YHRLLRDLLLIVTRIVELL (SEQ ID NO:121)
YHRLRDLLLIVTRIVELL (SEQ ID NO:122)
RRGLLEVIRTVILPRRLLDRL (SEQ ID NO:123)
YHRLRDLALIVTRIVELL (SEQ ID NO:124)
RRGLLRVIRTVILALDIL (SEQ ID NO:125)
RRGLLEVIRTVILLLDRLRHY (SEQ ID NO:126)
RRGLLEVIRTVILALDRLRHY (SEQ ID NO:127)
RRGLLEVIRTVILALDRL (SEQ ID NO:128)
YHRLRDLLLIVCRIVELL (SEQ ID NO:129)
YHRLRDLLLIVCRIVELLGRR (SEQ ID NO:130)
YHRLRDLLLIVTRIVELLGRR (SEQ ID NO:131)
RRGLLEVIRCVILLLDRL (SEQ ID NO:132)
RRGLLRVIRTVILLLDRL (SEQ ID NO:133)
RRGLLEVIRTVILLLRRL (SEQ ID NO:134)
RRGLLEVIRCVILLLDRLRHY (SEQ ID NO:135)
RRGLLRVIRTVILLLDRLRHY (SEQ ID NO:136)
RRGLLEVIRTVILLLRRLRHY (SEQ ID NO:137)
YHKLKLLLIVTKIVELLGKK (SEQ ID NO:138)
SLP2A ANALOGS

FLIRQLIRQLLTWQPILQYILQ (SEQ ID NO:139)
FLIRQLIRLLTWLFSNCRTLLSEVY (SEQ ID NO:140)
FLIRQLIRLLTWLFSNCRTLL (SEQ ID NO:141)
LLTRCNSFLWTLLRILQRILF (SEQ ID NO:142)
FLIRQLIRLLTWLFPNCRTLLSRVY (SEQ ID NO:143)
YVRSLLTRCNSFLWTLLRILQRILF (SEQ ID NO:144)
FLIKQLIKLLTWLFSNCKTLLSKVY (SEQ ID NO:145)
SLP2B ANALOGS

RLVERIRQLTASRQLIPQLIQYV (SEQ ID NO:146)
RLVRRIRQLTASRQLIPQLIQYV (SEQ ID NO:147)
LLSRVYQILQPILQRLSATLQAIREVL (SEQ ID NO:148)
LLSRVYQILQPILQRLCATLQRIREVLR (SEQ ID NO:149)
RLVERIRQLTASLRQLIPQLIQYVRSLL (SEQ ID NO:150)
LLSKVYQILQPILQKLSATLQKIKEVLK (SEQ ID NO:151)
SLP2 REGION ANALOGS

RLLTWLFSNCRTLLSRVYQILQPIL (SEQ ID NO:152)
RLLTWLFSNRRTLLSRVYQILQEIL (SEQ ID NO:153)
RLLTWLRRTLLSRVYQILQEIL (SEQ ID NO:154)
ELP ANALOGS

RIAGYGLRGLAVIIRCIIRGLNLIFEIIR (SEQ ID NO:155)
RIAGYGLRGLAVIIRIICRGLNLIFEIIR (SEQ ID NO:156)
RIAGYGLRGLAVIPRRICIRGLNLIFEIIR (SEQ ID NO:157)
RIIEFILNLGRICIRIIVALGRLGYGAIR (SEQ ID NO:158)
KIAGYGLKGLAVIIKICIKGLNLIFEIIK (SEQ ID NO:159)

Preferably, the antimicrobial peptides of the invention have the following structural formulae:
FLIRQLIRLLTWLFSNCRTLLSRVY (SEQ ID NO:4);
LLSRVYQILQPILQRLSATLQRIREVLR (SEQ ID NO:5);
RVIEVVQGACRAIRHIPRRIR (SEQ ID NO:7);
VVQGACRAIRHIPRRIR (SEQ ID NO:8); and
GACRAIRHIPRRIR (SEQ ID NO:9).

Analogs and homologs of other naturally occurring lytic peptides derived from other lentivirus proteins are also within the scope of the invention. Peptides may be derived from proteins of any lentivirus or any DNA or RNA virus including, but not limited to, HIV-1, HIV-2, SIV, EIAV, feline immunodeficiency virus (FIV), bovine immunodeficiency virus (BIV), visna virus and all clades, subclasses and isolates thereof.

Peptides can be synthesized according to classic Merrifield solid phase synthesis techniques, using manual or automated procedures known to those skilled in the art, e.g., as described by Miller et al. (AIDS Res. and Hum. Retro. 7: 511–519, 1991), using an Advanced Chemtech model 200 (Advanced Chemtech, Louisville, Ky.), or using a Millipore 9050+ (Millipore, Bedford, Mass.) automated synthesizer with Fmoc synthesis protocols (Fontenot et al., Peptide Research 4: 19–25, 1991), or other available instrumentation. After cleavage and deprotection, synthetic peptides can be purified by, for example, gel filtration chromatography and any reverse-phase column/HPLC system known to those skilled in the art.

Peptides may also be prepared by standard recombinant DNA technology using techniques well known to those skilled in the art for nucleotide-based peptide design (Sambrook et al., *Molecular Cloning: A Laboratory Manual*, 2nd edition (Cold Spring Harbor Press, Cold Spring Harbor, N.Y.; Ausubel et al., *Current Protocols in Molecular Biology*, John Wiley and Sons, New York, 1995). Site-directed mutagenesis, for example, may be used to prepare peptide analogs and homologs from parent peptides.

The amino acid sequences of the peptides can also be confirmed and identified by amino acid composition analysis as well as manual and automated Edman degradation and determination of each amino acid, HPLC analysis, or mass spectrometry.

The N-terminal amino acid of the peptides may contain a free amino group or be acetylated, and the C-terminal amino acid of the peptide may be amidated or comprise a free carboxy group. Other modifications of the peptide termini known to those skilled in the art are within the scope of the invention.

The criticality of particular amino acid residues in a peptide may be tested by altering or replacing the residue of interest. For example, the requirement for a cysteine residue, which can be involved in the formation of intramolecular or intermolecular disulfide bonds, can be tested by mutagenesis of the cysteine to another amino acid, for example, tyrosine, which cannot form such a bond. A cysteine can be chemically altered so as to prevent the formation of a disulfide bond by, for example, reduction and carboxyamidation, in which an amide group is added to the sulfur atom of the cysteine (Creighton, T. E., ed., *Protein Structure: A Practical Approach*, IRL Press, Oxford, 1989). Conversely, a cysteine residue in a peptide may be maintained in an oxidized state (that is, in the form of a disulfide bond) in order to assess whether such bonds are involved in the antimicrobial activity of a peptide. Such oxidation may be performed by, for example, an air-oxidation procedure (Ellman, G. L., Arch. Biochem. 82: 70–77, 1959), or by DMSO oxidation (Tam et al., J. Am. Chem. Soc. 113: 6657–6662, 1991).

Computer modeling is used to design antimicrobial peptides of the invention based on their preferred structural properties. The standard method for prediction of amphipathic helical structure from a linear sequence uses the Eisenberg algorithm (Eisenberg et al., Biopolymers 27: 171–177, 1990). Peptide sequences are analyzed for predicted secondary structure, hydrophobic moment, and amphipathicity using the Genetics Computer Group (Madison, Wis.) package of programs through the Pittsburgh Super Computer Facility. Predictive algorithms for secondary structure (Chou et al., Adv. Enz. 47: 45–146, 1978; Garnier et al., J. Mol. Biol. 120: 97, 1978) or hydrophobic moment (Eisenberg et al., Proc. Natl. Acad. Sci. U.S.A. 81: 140–144, 1984) may be used.

Peptide concentration is quantitated using a standard ninhydrin colorimetric assay. A standard curve using 1.0 mM leucine is generated by reading the spectrophotometric absorbance at 570 nm of increasing volumes of the leucine stock combined with the commercially available (Dupont) ninhydrin reagents on a spectrophotometer. The readings of peptide samples are compared to the leucine standard curve to quantitate the amount of peptide in each sample.

The effect of the antimicrobial peptides of the invention on the viability of procaryotic and eucaryotic cells may be assayed by any method which determines survival after treatment or exposure to the peptides. Preferably, the peptides of the invention are characterized using standard in vitro assays.

The antibacterial properties of the peptides of the present invention may be determined from a bacterial lysis assay (see, e.g., EXAMPLE 1), as well as by other methods, including, inter alia, growth inhibition assays (Blondelle et al., Biochemistry 31: 12688, 1992), fluorescence-based bacterial viability assays (e.g., Molecular Probes BacLight), flow cytometry analyses (Arroyo et al., J. Virol. 69: 4095–4102, 1995), and other standard assays known to those skilled in the art.

Determination of the antifungal properties of the peptides of the invention may be performed by techniques well known to those skilled in the art (Selitrennikoff, C., Screening for Antifungal Drugs, in *Biotechnology of Filamentous Fungi*, Finkelstein et al., eds., Butterworth-Heinemann, Boston, 1992).

Determination of the antiviral properties of the peptides of the invention may be performed by techniques well known to those skilled in the art, for example by the ability of a peptide to inhibit viral plaque formation in standard in vitro assays (e.g. Wild et al., Proc. Natl. Acad. Sci. USA 89: 10537–10541, 1992).

The assays for growth inhibition of a microbial target can be used to derive an $LD_{50}$ value for the peptide, that is, the concentration of peptide required to kill 50% of the microbial sample being tested. Alternatively, growth inhibition by an antimicrobial peptide of the invention may also be characterized using the minimum inhibitory concentration (MIC), which is the concentration of peptide required to achieve a defined percentage of inhibition. Such values are well known to those in the art as representative of the effectiveness of a particular antimicrobial agent (e.g., an antibiotic) against a particular organism or group of organisms.

In assays to detect the antibacterial activity of a peptide, growth inhibition of a bacterial population also can be measured with reference to the number of colony forming units (CFU) after exposure to a peptide relative to a control experiment without a peptide. Cytolysis of a bacterial population by an antimicrobial peptide can also be characterized by the minimum bactericidal concentration (MBC), which is the concentration required to reduce the viable bacterial population by 99.9%. The value of $MBC_{50}$ can also be used, defined as the concentration of a peptide required to reduce the viable bacterial population by 50%. In assays where log killing is plotted as a function of peptide concentration, log killing is defined as:

$$\log \frac{[\#CFU \times \text{dilution (control)}]}{[\#CFU \times \text{dilution (peptide-treated)}]}$$

In assays where zero colonies remain after treatment with a peptide, log killing can be estimated and termed as complete killing.

Another parameter useful in identifying and measuring the effectiveness of the antimicrobial peptides of the invention is the determination of the kinetics of the antimicrobial activity of a peptide. Such a determination can be made by performing any of the assays of the invention and determining antimicrobial activity as a function of time. In a preferred embodiment, the peptides display kinetics which result in efficient lysis of a microorganism.

The antimicrobial peptides of the invention display selective toxicity to target microorganisms and minimal toxicity to mammalian cells. Determining the effect of a peptide of the invention on mammalian cells is preferably performed using tissue culture assays. For mammalian cells, such assay methods include, inter alia, trypan blue exclusion and MTT assays (Moore et al., Peptide Research 7: 265–269, 1994). Where a specific cell type may release a specific metabolite upon changes in membrane permeability, that specific metabolite may be assayed, e.g., the release of hemoglobin upon the lysis of red blood cells (Srinivas et al., J. Biol. Chem. 267: 7121–7127, 1992). The peptides of the invention are preferably tested against primary cells, e.g., using human skin fibroblasts (HSF) or fetal equine kidney (FEK) cell cultures, or other primary cell cultures routinely used by those skilled in the art. Permanent cell lines may also be used, e.g., Jurkat cells.

In determining the therapeutic potential of a candidate peptide, one that exhibits a lower MBC or $MBC_{50}$ for bacterial, fungal, protozoal or viral samples relative to that observed for mammalian cells is defined as selectively antimicrobial.

Characterization of the antimicrobial activity of the peptides of the invention can be performed using any microorganism which can be cultured and assayed, as above, including bacteria, fungi, protozoa or viruses.

Antibacterial assays for the peptides of the invention can be performed to determine the bacterial activity toward both Gram-positive and Gram-negative microorganisms. *Escherichia coli* and *P. aeruginosa* are examples of Gram-negative organisms. *P. aeruginosa* is a particularly problematic source of disease in such conditions as cystic fibrosis, burn infections, eye and urinary tract infections. *S. aureus* may be used as a model of a Gram-positive microorganism, and this is a significant clinical target as well because it is refractive to most systemic antibiotic treatments. Methicillin-resistant *S. aureus* may be used as an antibiotic-resistant model organism. *E. faecalis* can be assayed, and in particular, the vancomycin-resistant isolates found in clinical settings such as a hospital. *S. marcescens* is a source of ophthalmic and other topical infections, and can be readily assayed. The peptides may be used in the treatment of external ear infections (otitis externa), or in the treatment of sexually transmitted diseases such as *Niesseria gonorrhea* and trichomonas infections.

Other bacterial pathogens, often found extracellularly on mucosal surfaces, which may be targets for the peptides of the present invention included, but are not limited to, *Streptococcus pneumonia, Streptococcus pyogenes*, Group B Streptococci, *Corynebacter diphtheriae, Gardnierella vaginalis, Klebsiella pneumoniae*, Acinetobacter spp., *Bordetella pertussis, Haemophilus aegyptius, Haemophilus*

*influenzae, Haemophilus ducreyi, S. epidermis,* Shigella spp. Serratia spp., and *Propionibacterium acnes.* Other microbial pathogens which may be targets for the peptides of the present invention include, but are not limited to, *Chlamydia trachomatis,* Mycoplasma spp. especially *M. pneumoniae,* and Bacteriodes spp., as well as others known to those skilled in the art.

Fungi also may be susceptible to specific peptides of the invention because their membranes contain ergosterol, which is not found in human cells. This differentiation may be exploited in therapeutic applications so as to design peptides of the invention which selectively inhibit fungi, yet do not interfere with human or mammalian membrane function. Precedent for a mechanism of selective antifungal membrane targeting is found, for example, in the use of the antifungal agent, amphotericin B, which binds ergosterol and forms pores in the membrane (Goodman et al., *The Pharmacological Basis of Therapeutics,* Macmillan Publishing, New York, 1985). All fungi can be considered as potential targets of these peptides, including, but not limited to, dermatophytes, yeasts, dimorphic fungi, and filamentous molds. Specific fungal pathogens which may be targets for the peptides of the present invention include, but are not limited to, Microsporum spp., Epidermophytom spp., *Candida albicans, Cryptococcus neoformans,* Trichophytom spp., *Sporothrix schenki* and *Aspergillus fumigatus,* as well as other pathogens known to those skilled in the art.

Both DNA and RNA viruses can be targets of the antimicrobial peptides of the invention. In a particular embodiment of the invention, an enveloped virus may be susceptible to the antiviral effect of the peptides due to the ability of these peptides to target and disrupt membrane structures. While all viruses are potential targets, such enveloped viruses as poxvirus, herpesvirus, hepadnavirus, baculovirus, orthomyxovirus, paramyxovirus, retrovirus, togavirus, rhabdovirus, bunyavirus and flavivirus, for example, may be particularly susceptible to the antimicrobial peptides of the invention.

Additionally, further elucidation of the mechanism of the peptides and their biochemical targets may come from the use of isogenic mutants of bacteria, fungi and viruses that are altered in cytoplasmic and outer wall membrane content. Peptide analogs of the invention may be specifically tested against these mutants to identify specific designs that are optimally inhibitory against particular membrane constituents.

The evaluation of an antimicrobial peptide of the invention for inhibiting or treating a particular microbial infection may also involve the use of animal models of infection that are acknowledged by those skilled in the art to be relevant to such infections in a human or other mammal.

Advantages of the use of these analogs as antibiotics include the likelihood that it may be more difficult for a microorganism to develop a mechanism of resistance against an antibiotic which targets a membrane structure. Furthermore, the size of the peptides make them relatively simple to prepare by standard synthetic peptide chemistry, an attractive feature for production level scale-up.

In view of the above noted properties of the peptides of the invention, it is contemplated that the antimicrobial peptides of the invention may be used in combatting and/or eliminating an infectious process in a host caused by a microorganism. Another aspect of the invention is directed to methods for eliminating an infectious process by administering the peptides of the present invention to a patient for a time and under conditions to promote healing. In a particular aspect of the invention, the high potency and rapid bactericidal activity of these peptides make them attractive candidates for use in preventative therapies, such as sterilization of wounds prior to suture, as well as the sterilization of instruments prior to their use in surgical or other invasive procedures. Their microbial specificity renders the peptides of the invention particularly useful in inhibiting unwanted microbial growth in tissue culture, especially those used for production of recombinant proteins or vectors for use in gene therapy. In another embodiment of the invention, the peptides may be used in combination formulations with one or more other drugs to facilitate delivery of a drug into a host cell or microorganism.

The invention is also directed to pharmaceutical compositions containing one or more of the antimicrobial peptides of the invention as the active ingredient which may be administered to a host in need of such a composition in a therapeutically effective amount, an amount of the peptide (or combinations of peptides) sufficient to minimize or eliminate the target microorganism from a cell culture, or host individual. The pharmaceutical compositions contain a therapeutically effective dosage of at least one of the antimicrobial peptides according to the present invention, together with a pharmaceutically acceptable carrier.

The invention is also directed to methods for treating a microbial infection in a host using the compositions of the invention. Such treatment comprises the administration of a pharmaceutical composition of the invention in a therapeutically effective amount to an individual in need of such treatment. The compositions may be administered parenterally by intramuscular, intravenous, or subcutaneous routes; orally, topically and intranasally. The invention is directed to the treatment of infections caused by such microorganisms as *S. aureus, S. marcescens, P. aeruginosa, E. faecalis, E. coli,* fungi, protozoa and viruses in any mammalian host.

Preferably, pharmaceutical compositions containing the peptides of the invention are applied topically for the elimination of surface infections caused by microorganisms. When used in a topical pharmaceutical composition, the peptide active ingredient can be used at a concentration of 0.001 to 20%.

When applied topically, the peptide compositions may be combined with other ingredients, such as carriers and/or adjuvants. The peptides may also be covalently attached to a protein carrier, such as albumin, so as to minimize diffusion of the peptides. There are no limitations on the nature of such other ingredients, except that they must be pharmaceutically acceptable, efficacious for their intended administration and cannot degrade the activity of the active ingredients of the compositions. When the peptide compositions of this invention are applied to a site of topical infection, they may be in the form of an irritant. The peptide compositions can also be in the form of ointments or suspensions, preferably in combination with purified collagen. The peptide compositions also may be impregnated into transdermal patches, plasters and bandages, preferably in a liquid or semi-liquid form.

The peptides of the invention may also be systematically administered for promoting the healing of an infectious process. When applied systemically, the peptide compositions may be formulated as liquids, pills, tablets, lozenges or the like, for enteral administration, or in liquid form for parenteral injection. The peptides (or peptide-protein conjugates) may be combined with other ingredients such as carriers and/or adjuvants. There are no limitations on the nature of such other ingredients, except that they must be pharmaceutically acceptable, efficacious for their intended administration and cannot degrade the activity of the active ingredients of the compositions.

The pharmaceutical forms suitable for injection include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water buffered aqueous solutions (i.e., biocompatible buffers), ethanol, polyol such as glycerol, propylene glycol, polyethylene glycol, suitable mixtures thereof, surfactants or vegetable oils. Sterilization can be accomplished by an art-recognized technique, including but not limited to, filtration or addition of antibacterial or antifungal agents, for example, paraben, chlorobutanol, phenol, sorbic acid or thimerosal. Further, isotonic agents such as sugars, for example, may be incorporated in the subject compositions.

Production of sterile injectable solutions containing the subject peptides is accomplished by incorporating these compounds in the required amount in the appropriate solvent with various ingredients enumerated above, as required, followed by sterilization, preferably filter sterilization. To obtain a sterile powder, the above solutions are vacuum-dried or freeze-dried as necessary.

When the peptides of the invention are administered orally, the pharmaceutical compositions thereof containing an effective dosage of the peptide may also contain an inert diluent, an assimilable edible carrier and the like, be in hard or soft shell gelatin capsules, be compressed into tablets, or may be in an elixir, suspension, syrup or the like.

The subject peptides are thus compounded for convenient and effective administration in pharmaceutically effective amounts with a suitable pharmaceutically acceptable carrier in a therapeutically effective dosage.

The precise therapeutically effective amount of peptides to be used in the methods of this invention to control infection can be determined without undue experimentation by those skilled in the art who understand the nature of the activity of antibiotics and the nature of an infectious process. The amount of an antibiotic peptide (such as the peptides of this invention) that must be utilized will vary with the magnitude of the infection and the microorganism to be treated.

The amount of peptide of the invention per unit volume of combined medication for administration may also be determined without undue experimentation by those skilled in the art. However, it can generally be stated that the peptides should preferably be present in an amount of at least about 1.0 nanogram per milliliter of combined composition, more preferably in an amount up to about 1.0 milligram per milliliter.

Systemic dosages also depend on the age, weight and conditions of the patient and on the administration route. For example, a suitable dosage for the administration to adult humans can range from about 0.01 to about 100 mg per kilogram body weight. The preferred dosage can range from about 0.5 to about 5.0 mg per kilogram body weight.

As used herein, a pharmaceutically acceptable carrier includes any and all solvents, dispersion media, coatings, and the like. The use of such media and agents are well-known in the art.

Because the antimicrobial peptide compositions of this invention are designed to eliminate an ongoing infectious process, a continual application or periodic reapplication of the compositions is indicated and preferred.

The practice of the invention employs, unless otherwise indicated, conventional techniques of synthetic organic chemistry, protein chemistry, molecular biology, microbiology, recombinant DNA technology, and pharmacology, which are within the skill of the art. Such techniques are explained fully in the literature. See, e.g., Scopes, R. K. *Protein Purification: Principles and Practices,* 2nd edition (Springer-Verlag, 1987); Methods in Enzymology (S. Colwick and N. Kaplan, editors, Academic Press); Sambrook et al., *Molecular Cloning: A Laboratory Manual,* 2nd edition (Cold Spring Harbor Press, Cold Spring Harbor, N.Y.); Ausubel et al., *Current Protocols in Molecular Biology,* John Wiley and Sons, New York, 1995; *Remington's Pharmaceutical Sciences,* 17th ed., Mack Publishing Co., Easton, Pa., 1985.

The following examples further illustrate the invention, but are not meant to limit same.

EXAMPLE 1

Synthesis of Antimicrobial Peptides and Analogs

Structural Analysis of Peptide Sequences. Viral envelope protein sequences of SIV and HIV-1 were analyzed for predicted secondary structure (Chou et al., Biochemistry 13: 222–245, 1974), hydrophobic moment (Eisenberg et al., J. Mol. Biol. 179: 125–142, 1984), and amphipathicity using the Genetics Computer Group (Madison, Wis.) package of programs through the Pittsburgh Super Computer. Peptides were chosen for synthesis based on the identification of the above characteristics in the protein sequence (arginine-rich, hydrophobic-rich, and predicted to form amphipathic $\alpha$-helices).

Peptide Synthesis. Peptides were synthesized as described previously (Fontenot et al., Peptide Research 4: 19–25, 1991; Miller et al., AIDS. Res. Hum. Retroviruses 7: 511–519, 1991) using either an Advanced Chemtech model 200 (Advanced Chemtech, Louisville, Ky.) or a Millipore 9050+ (Millipore, Bedford, Mass.) automated peptide synthesizer with Fmoc synthesis protocols. After cleavage and deprotection, synthetic peptides were characterized and purified by reverse-phase HPLC on Vydac C18 or C4 columns (The Separations Group, Hesperia, Calif.). The identity of each peptide was confirmed by mass spectrometry (University of Pittsburgh Protein & Peptide Core Facility). Magainin 2 was purchased from Calbiochem (San Diego, Calif.) and used without further purification. For reduction and carboxyamidation of peptides for blocking cysteine —SH— groups, a 1 mM solution of peptide in 20 mM Tris, pH 8.2, was used. DTT was added to a concentration of 1 mM, and the solution was allowed to stand at room temperature for 15 minutes. A 0.2M iodoacetamide solution was used to add this reagent to a concentration of 2 mM. The solution was mixed well and incubated for 15 minutes at room temperature in the dark. The reaction mixture was dialyzed against water (Creighton, T. E., ed., *Protein Structure: A Practical Approach,* IRL Press, Oxford, 1989).

The oxidation of cysteine residues was performed by dissolving a peptide in water at a concentration of approximately 1 mg/ml. The pH of this solution was adjusted to pH 8–9 using acetic acid and ammonium hydroxide. The solution was covered lightly and stirred vigorously in air for several days. The pH was checked each day and adjusted. The reaction was monitored by high performance liquid chromatography (HPLC) or, alternatively, the Ellman test (Ellman, Arch. Biochem. 82: 70–77, 1959). Upon the completion of the reaction, the peptide was lyophilized to dryness.

Peptide Quantitation. Peptide concentrations were determined by quantitative ninhydrin assay. Briefly, to samples containing 5–60 nmol peptide, Ninhydrin Reagents A, B, and C (purchased from Dupont or made as described by Sarin et al. (Sarin et al., Anal. Biochem. 117: 147–157, 1981) were added; standards consisting of 0–60 nmol leucine were prepared in parallel for use as a standard. The purple color formed upon incubation at 100° C. for 10 min was quantitated by dilution in 1:1 isopropanol/water, transfer to triplicate wells of a 96-well plate, and measurement of the $A_{570}$ on a microwell plate reader (Dynatech, Chantilly, Va.). The results were confirmed by routine amino acid composition analysis of both the leucine standard and peptide solutions.

Peptide Sequences. Table 2 lists the structural formulae of the peptides used in the studies described below. The peptide sequences fall into the following categories: natural (those corresponding to amino acid sequences derived from regions of lentivirus transmembrane proteins); engineered, possessing 1 or 2 amino acid substitutions compared to the corresponding natural sequence; truncated, having 6–14 residues removed from either end of the natural or "parent" LLP1 sequence; and modified, having been either reduced and carboxyamidated (LLP1-Am) or gently oxidized to form a disulfide-linked dimer (bis-LLP1).

viruses 7: 511–519, 1991). Bacterial suspensions were cultured in Luria Broth to mid-log growth phase and washed by several cycles of centrifugation and resuspension in 10 mM phosphate buffer. The $A_{600}$ of the suspension was adjusted with 10 mM phosphate buffer such that, upon dilution, $5–10\times10^5$ CFU/ml would be treated in the assay. Bacteria were incubated with two-fold dilutions of peptides (32–0.1 μM) in 96-well plates in 10 mM phosphate buffer, pH 7.2, for 1 hour. Ten-fold dilutions were performed to a dilution of 1:1000; a 100-μl aliquot from each condition was plated on tryptic soy agar (Difco, Detroit, Mich.) and the plates were incubated overnight. Colonies of surviving bacteria (colony-forming units) were counted and compared to untreated controls to determine the amount of peptide-induced killing under each condition. Log killing is defined as the log of the ratio of CFUs present before and after treatment with peptide. Complete killing is indicated where there were zero colonies per 100-μl aliquot of undiluted bacteria-peptide mixture.

Calculation of MBC. To quantitate bactericidal activity, MBC values were determined by a method similar to that above, except that duplicate 10-μL aliquots of only undiluted peptide-bacteria cultures (32–0.25 μM peptide) were plated

TABLE 2

Structural Formulae of Peptides Used in Antimicrobial Assays

| Peptide Name | Amino Acid Sequence | Sequence Source[1] |
|---|---|---|
| LLP1 (SEQ ID NO: 1) | RVIEVVQGACRAIRHIPRRIRQGLERIL | HIVHXB2R 828-855 |
| LLP2 (SEQ ID NO: 2) | YHRLRDLLLIVTRIVELLGRR | HIVHXB2R 768-788 |
| SLP1 (SEQ ID NO: 3) | DLWETLRRGGRWILAIPRRIRQGLELTL | SIVMM239 852-879 |
| SLP2 (SEQ ID NO: 4) | FLIRQLIRLLTWLFSNCRTLLSRVY | SIVMM239 771-795 |
| SLP2B (SEQ ID NO: 5) | LLSRVYQILQPILQRLSATLQRIREVLR | SIVMM239 790-817 |
| ELP (SEQ ID NO: 6) | RIAGYGLRGLAVIIRICIRGLNLIFEIIR | EIAV 808-836 (Wyoming) |
| Analog 5 (SEQ ID NO: 160) | RVIRVVQGACRAIRHIPRRIRQGLRRIL | engineered analog of LLP1 |
| Analog 3 (SEQ ID NO: 161) | RVIEVVQGACRAIEHIPRRIEQGLERIL | engineered analog of LLP1 |
| R841E (SEQ ID NO: 162) | RVIEVVQGACRAIEHIPRRIRQGLERIL | engineered analog of LLP1 |
| R848E (SEQ ID NO: 163) | RVIEVVQGACRAIRHIPRRIEQGLERIL | engineered analog of LLP1 |
| I840S (SEQ ID NO: 164) | RVIEVVQGACRASRHIPRRIRQGLERIL | engineered analog of LLP1 |
| I847S (SEQ ID NO: 165) | RVIEVVQGACRAIRHIPRRSRQGLERIL | engineered analog of LLP1 |
| SLP2A1 (SEQ ID NO: 166) | FLIRQLIELLTWLFSNCRTLLSEVY | engineered analog of SLP2A |
| SLP2B1 (SEQ ID NO: 167) | LLSEVYQILQPILQELSATLQRIREVLR | engineered analog of SLP2B |
| LLP2A3 (SEQ ID NO: 168) | YHELRDLLLIVTRIVELLGRE | engineered analog of LLP2 |
| LP21 (SEQ ID NO: 7) | RVIEVVQGACRAIRHIPRRIR | HXB2R 828-848 (HIV) |
| LP17 (SEQ ID NO: 8) | VVQGACRAIRHIPRRIR | HXB2R 832-848 (HIV) |
| LP14 (SEQ ID NO: 9) | GACRAIRHIPRRIR | HXB2R 835-848 (HIV) |
| C837Y (SEQ ID NO: 169) | RVIEVVQGAYRAIRHIPRRIRQGLERIL | MFA 828-855 (HIV) |
| LLP1-Am (SEQ ID NO: 10) | RVIEVVQGACRAIRHIPRRIRGQLERIL | LLP1 with chemically modified cysteine |
| | X | |
| bis-LLP1 (SEQ ID NO: 11) | RVIEVVQGACRAIRHIPRRIRQGLERIL | disulfide-linked dimer of LLP1 |
| | RVIEVVQGACRAIRHIPRRIRQGLERIL | |
| magainin 2 | GIGKFLHSAKKFGKAFVGEIMNS | natural antibiotic peptide |

[1]Sequences of the family of LLPs derived from HIV and SIV envelope proteins are consistent with the numbering in Myers. The sequence of ELP, the peptide derived from the ENV protein of EIAV, is from the Wyoming strain (Rushlow et al., 1986).

EXAMPLE 2

Antibacterial Assays of Antimicrobial Peptides

Methods

Bacterial lysis assay. Bacterial lysis assays were conducted in a manner similar to that described previously (Lehrer, R. I., M. E. Selsted, D. Szklarek, and F. J. 1983. Infect. Immun. 42: 10–4, 1983; Miller, M. A., R. F. Garry, J. M. Jaynes, and R. C. Montelaro, AIDS Res Hum Retroand counted. The minimal bactericidal concentration, MBC, is the peptide concentration at which 99.9% (3 logs) killing is achieved (Pearson et al., Antimicrob. Agents Chemother. 18: 699–708, 1980). The $MBC_{50}$ is the peptide concentration at which 50% killing is achieved.

Kinetics of Bacterial Killing. The time course of the cytolytic activity of a peptide was determined by a modification of the above procedure, where a volume of appropriately diluted bacteria was treated with 1–10 μM peptide;

aliquots of this mixture were removed every 10 seconds and diluted 1:2 in 2× Luria Broth; each resulting suspension was subsequently plated on agar as described above. The number of colonies visible upon incubation for each time point was used to calculate a rate of killing by the peptide.

Erythrocyte Lysis Assay. Peptides were screened for hemolytic activity by treating freshly isolated human red blood cells (RBC) with various concentrations of peptides, centrifuging the samples to pellet intact cells, and measuring the amount of hemoglobin in the supernatant to determine the extent of RBC lysis under each condition. The method used is essentially that described by Srinivas et al. (J. Biol. Chem. 267: 7121–7127, 1992) with the following modifications: peptide concentrations of 0.1–100 µM were tested, the incubation period was 1 hour at 37° C., and the $A_{570}$ was measured in duplicate wells of a 96-well plate. A calibration curve was constructed by treating various amounts of red blood cells (0, 20,40, 60, 80, and 100% of the volume of RBC used in test samples) with plain water, which completely lyses the cells. The standard curve was used to calculate the percent lysis at each peptide concentration.

Jurkat cells. Jurkat cells (human T-lymphocytes) were incubated with various concentrations of test peptides over a two day period. Live cells were counted at 24 hour intervals using trypan blue exclusion and plotted as a function of peptide concentration in order to determine the peptide concentration resulting in 50% fewer viable cells compared to the controls.

Test Samples. The panel of bacterial isolates used for these experiments includes both Gram-positive and Gram-negative strains, as well as two known antibiotic-resistant strains, and are described in Table 3.

TABLE 3

Bacterial Strains Used in LLP1 Susceptibility Studies

| Organism Name | Designation | Characteristics |
| --- | --- | --- |
| Pseudomonas aeruginosa | RW1 | laboratory-passaged urinary tract isolate |
| Staphylococcus aureus | RW2 | laboratory-passaged clinical isolate |
| Staphylococcus aureus | WP96146 | Methicillin-resistant clinical isolate |
| Enterococcus faecalis | WP1 | Clinical isolate |
| Enterococcus faecalis | WP2 | Vancomycin-resistant clinical isolate |
| Serratia marcescens | SK4056 | Clinical isolate from a wound |
| Serratia marcescens | SK231224 | Clinical isolate from a toe |

Results

Table 4 shows the potencies and selectivities of the parent antimicrobial peptides of the invention. In order to determine the antimicrobial activity of the test peptides, LLP1 was compared on a molar basis with magainin 2 in a standard bacterial killing assay. Various concentrations of each peptide were incubated with *S. aureus* for one hour; this treatment resulted in a dose-dependent reduction in colony-forming units (CFU) of bacteria (FIG. 1). At and above 2.5 µM LLP1, "complete" killing is observed; that is, there were zero CFU remaining per 100 µl bacteria-peptide mixture, which corresponds to the elimination of at least $5 \times 10^5$ CFU/ml by this concentration of peptide. Magainin 2, on the other hand, results in the reduction of only about 90% of CFU/ml at 10 µM. Thus, at equal peptide concentrations, LLP1 reduces viable bacteria counts by at least three orders of magnitude more than magainin 2. The other peptides corresponding to naturally occurring sequences have activities different from that of LLP1, as summarized in the table. As shown by the MBC values for each of these peptides against *S. aureus*, the LLP2 regions from both HIV and SIV are highly active in our antibacterial assay (LLP2, SLP2A, and SLP2B). Thus each of the peptides in this panel of naturally-occurring sequences is a potent antimicrobial agent. When one looks at their selectivity, however, differences among them are disclosed.

Selectivity, or the killing of bacteria to the exclusion of normal eukaryotic cells, is a highly desirable characteristic of an antimicrobial agent. The peptides were evaluated for their relative toxicity to bacteria and eukaryotic cells. LLP1 is hemolytic only at high concentrations of peptide ($LD_{50}$ = 20–40 µM), nearly two orders of magnitude higher than the $MBC_{50}$, the concentration of peptide that will kill 50% of treated bacteria. Below 10 µM very little lysis is observed, making this peptide a selective antibacterial agent. Examination of the hemolytic properties of the entire panel of LLPs (Table 4) reveals some variation in potency and selectivity among them. Both of the SLP2 peptides are potent inhibitors of bacterial growth, but SLP2A is also rather hemolytic. Thus selectivity varies among the panel, with LLP1 and SLP2B being the more selective peptides tested.

The toxicity of LLP1 to mammalian cells in tissue culture was also tested. Toxicity of the peptide to Jurkat cells in medium after 48 h was measured by trypan blue vital staining. The results using Jurkat cells are similar to those obtained in RBC, indicating that long-term culture in the presence of peptide does not have an additional cytopathic effect. These results demonstrate that many of the antimicrobial peptides described here kill bacteria at much lower concentrations than those required to cause damage to eukaryotic cells. The exception to this is ELP, which has high hemolytic activity in the absence of measurable bactericidal activity.

ELP is extremely hydrophobic, has a high glycine content, and has relatively few basic amino acids. Although it has little antibacterial activity, it is highly hemolytic.

TABLE 4

Potency and Selectivity of Various LLPs Against *S. aureus*

| Peptide Name | MBC(µM)[1] | $MBC_{50}$[2] | Erythrocyte $LD_{50}$[3] | Jurkat $LD_{50}$[4] |
| --- | --- | --- | --- | --- |
| LLP1 | 2–4 | 1–2 | 40 | 6 |
| LLP2 | 4 | 1 | 7 | |
| SLP1 | >16 | 8 | 40 | >8 |
| SLP2A | >32 | 4 | 2 | 4 |
| SLP2B | 1 | .25 | 5 | 6 |
| ELP | >10 | >10 | 10 | |

[1] the concentration of peptide (closest 2-fold dilution) required to reduce the bacterial population (CFU/ml) by 99.9%
[2] the concentration of peptide (closest 2-fold dilution) required to reduce CFU/ml by 50%.
[3] the concentration of peptide (as measured on plot of $A_{560}$ vs. peptide concentration) required to cause 50% hemoglobin release from treated RBC (1 hour incubation).
[4] reduction in viable cell counts after a 48-h incubation of peptide with cells.

Figure 3:
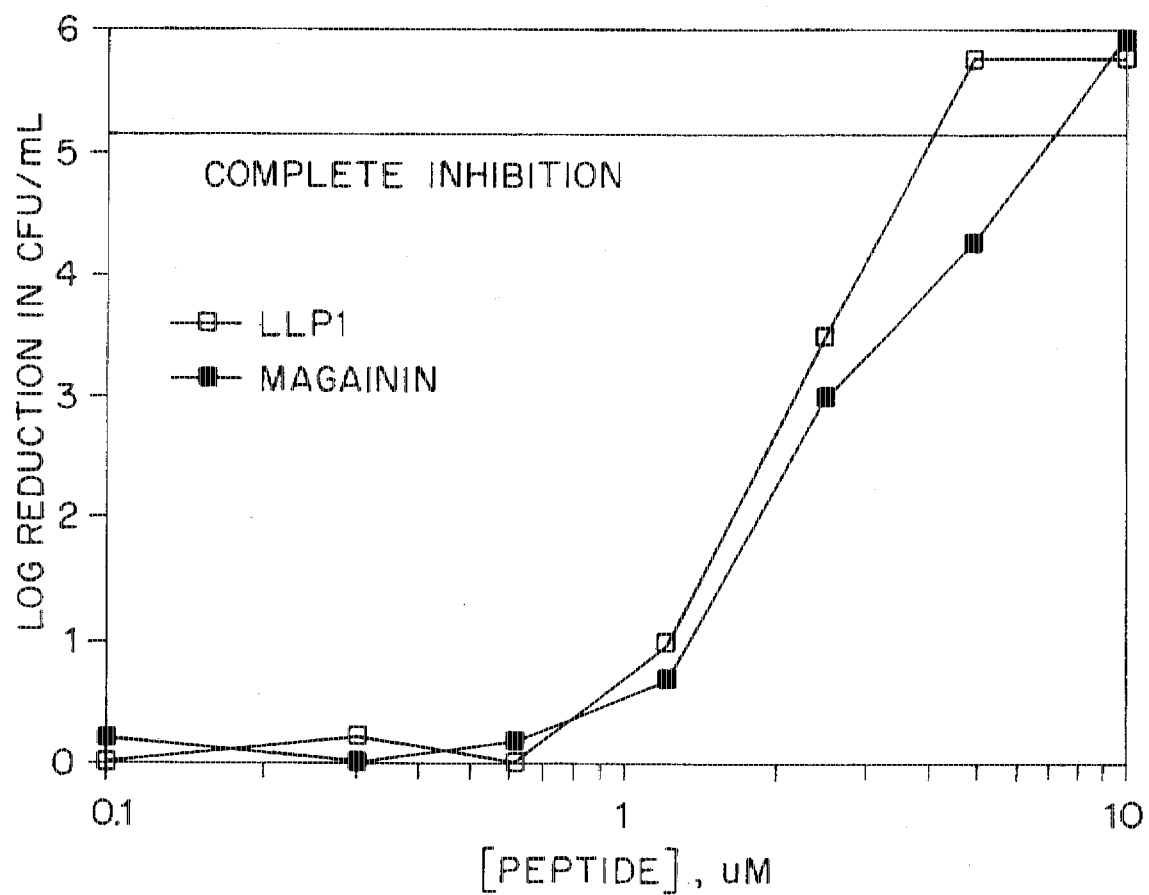
FIG. 3. shows growth inhibition of *Pseudomonas aeruginosa* by peptides LLP1 and magainin 2.

LLP1 was tested against Gram-negative pathogens to determine its spectrum of activity. *P. aeruginosa* is more susceptible to LLP1, although magainin is somewhat effective against this microbe (FIG. 3). LLP1 is highly bactericidal to *S. marcescens*, the other Gram-negative microbe tested, whereas magainin 2 is ineffective (Table 5). These data suggest that on a molar basis LLP1 is the more potent antibacterial agent. LLP1 is highly effective against both Gram-positive and Gram-negative bacterial pathogens. Magainin 2, by comparison, is ineffective at the concentrations tested against all strains except *P. aeruginosa*.

Figure 2:
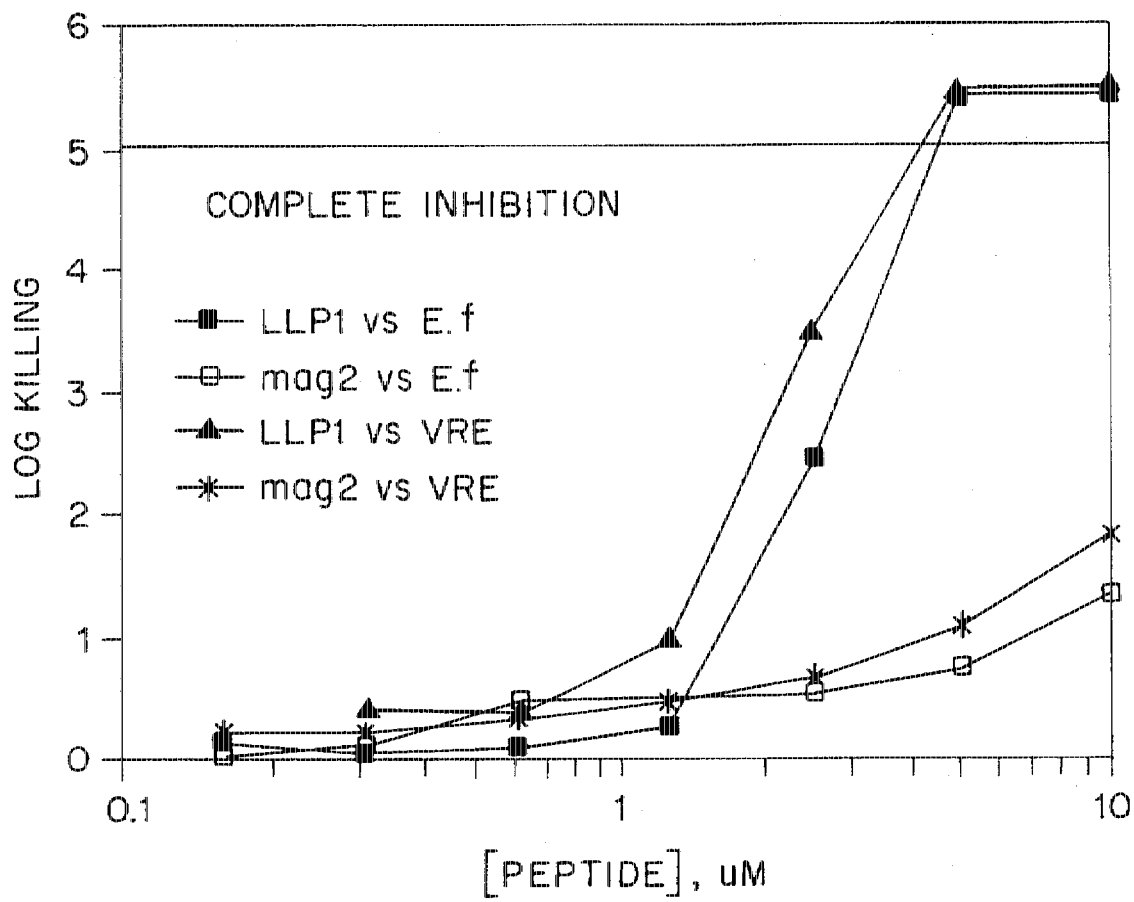
FIG. 2. shows growth inhibition of *Enterococcus faecalis* (EF) and vancomycin-resistant *Enterococcus faecalis* (VRE) by peptides LLP1 and magainin 2.

Known antibiotic-resistant strains of *S. aureus* and *E. faecalis* were tested for their susceptibility to LLP1 (Table 5 and FIGS. 1 and 2). The antibiotic-resistant pathogens are nearly equally as sensitive to LLP1 exposure as the corresponding susceptible strains. For example, LLP1 is two-fold more potent against a vancomycin-resistant strain of *E. faecalis* than a susceptible strain of this microbe. Similar results were obtained with the antibiotic-resistant strain of *S. aureus* tested, as well as several *S. marcescens* isolates with varying degrees of antibiotic resistance (data not shown). Magainin 2 is slightly more effective against the antibiotic-resistant strains of *S. auerus* and *E. faecalis*. These findings indicate that the antibiotic resistance mechanisms employed by these organisms do not greatly alter their susceptibility to either LLP1 or magainin 2.

TABLE 5

MBC of LLP1 and Magainin Against Various Bacterial Isolates

| Bacterial Strain | Pheno-type | MBC ($\mu M$)[1] LLP1 | magainin 2 | MBC$_{50}$ ($\mu M$)[2] LLP1 | magainin 2 |
|---|---|---|---|---|---|
| P. aeruginosa | | 2.5 | 5 | 1.3 | 1.3 |
| S. aureus | | 1.3–2.5 | >10 | .31–1.3 | >10 |
| S. aureus | Methi-cillin-resistant | 1.3–2.5 | >10 | .63–1.3 | 5–10 |
| E. faecalis | | 2.5–5 | >10 | 2.5 | 2.5 |
| E. faecalis | Vanco-mycin-resistant | 1.3–2.5 | >10 | .31 | .63 |
| S. marcescens | | 0.31–1.3 | >10 | .16–.31 | 2.5–5 |

[1]the concentration of peptide required to reduce the bacterial population (CFU/ml) by 99.9%.
[2]the concentration of peptide required to reduce the bacterial population (CFU/ml) by 50%.

Table 6 shows the antibacterial assays conducted with truncated peptides. A series of LLP1-truncated peptides (LP21, LP17, LP14) were tested against *S. aureus*. The results show that truncation of up to 14 residues from the C- or N-terminus of LLP1 results in a peptide with moderately reduced antibacterial but significantly reduced hemolytic properties. The hemolytic activity of each truncated peptide was less than 10% at 100 µM. Thus, the shorter peptides LP21, LP17 and LP14 maintain a high level of antibacterial activity but have virtually no hemolytic activity.

TABLE 6

Potency and Selectivity of LLP1 Truncated Analogs Against *S. aureus*

| Peptide Name | Length (AA) | MBC ($\mu M$)[1] | MBC$_{50}$[2] | Erythrocyte LD$_{50}$[3] |
|---|---|---|---|---|
| LLP1 | 28 | 2.5 | 1.25 | 40 |
| LP21 | 21 | 10 | 2.5 | >100 |

TABLE 6-continued

Potency and Selectivity of LLP1 Truncated Analogs Against *S. aureus*

| Peptide Name | Length (AA) | MBC ($\mu M$)[1] | MBC$_{50}$[2] | Erythrocyte LD$_{50}$[3] |
|---|---|---|---|---|
| LP17 | 17 | 20 | 5 | >100 |
| LP14 | 14 | 10 | 2.5 | >100 |

[1]the concentration of peptide (closest 2-fold dilution) required to reduce the bacterial population (CFU/ml) by 99.9%.
[2]the concentration of peptide required to reduce the bacterial population (CFU/ml) by 50%.
[3]the concentration of peptide (as measured on plot of A$_{560}$ vs peptide concentration) required to cause 50% hemoglobin release from treated red blood cells (RBC).

Table 7 describes the results of assays to determine the antimicrobial and hemolytic activity of analogs described in Table 2. The amino acid changes in these analogs may be classified as alterations in basic residues, hydrophobic residues, or cysteine. The functional effects of these changes were determined.

The potency of LLP1 can be altered by substitution of basic or acidic residues, resulting in a change in net charge of the peptide. This is demonstrated by the large differences in activity of Analog 5 and Analog 3 compared to LLP1. Analog 5 has two acidic to basic (Glu→Arg) substitutions and possesses very high antibacterial and hemolytic activity. Analog 3 possesses two basic to acidic (Arg→Glu) substitutions and is devoid of activity. This analog demonstrates that high positive charge correlates with antibacterial activity of the peptide. Single amino acid changes (e.g., peptides R841E and R848E) have a similar but less dramatic effect than the double substitution, reducing both the antibacterial and hemolytic activity of the peptides. Thus the sequences can be altered to achieve the potency desired. Basic to acidic changes appear to affect both antibacterial and hemolytic activities similarly.

Another type of substitution involves hydrophobic residues. Substitution of such residues by hydrophilic residues (e.g., I840S, I847S) also reduces antibacterial activity, suggesting that these residues are important for the activity of LLP1. However, the hemolytic activity of these peptides is significantly reduced, as evidence by the low amount of red blood cell lysis at 100 µM peptide. The antibacterial activity is higher than that of the (Arg→Glu) substituted peptides. Thus, a small reduction in the hydrophobicity of the peptide can result in a slightly less potent but more selective peptide. Such engineered changes are desirable to limit the toxicity of the antibacterial agent to normal eucaryotic cells.

When the sites of the substitutions in the parent peptides are analyzed, it appears that substitutions in the 847–848 region of LLP1 have a larger effect on function than those in the 840–841 region. The sequence PRRIR, residues 844–848, is highly conserved among HIV and SIV isolates, so it is likely that this sequence is very important to the function of the peptide. Analogs of SLP2A, SLP2B, and LLP2 were made containing two basic-to-acidic residue substitutions. Like the results from analog 3 of LLP1, this type of modification results in peptides with no antimicrobial or hemolytic activity. Thus the same type of substitutions used in the LLP1 analogs may be applied to the others with the expectation that the effects of such substitutions will be similar for each.

TABLE 7

Potency and Selectivity of LLP1 Substitution Analogs against *S. aureus*

| Peptide Name | MBC(μm)[1] | MBC$_{50}$[2] | Erythrocyte LD$_{50}$[3] | % lysis at 100 μM |
|---|---|---|---|---|
| Analog 3 | >80 | >80 | >100 | <5 |
| Analog 5 | 2.5 | 0.3 | 2 | 100 |
| R841E | 40–80 | 10–20 | >100 | 30 |
| R848E | 80 | 20 | >100 | 10 |
| I840S | 10–20 | 2.5 | >100 | <10 |
| I847S | 20 | 5 | >100 | <10 |
| SLP2A1 | >32 | >32 | >100 | 7 |
| SLP2B1 | >32 | >32 | >100 | 10 |
| LLP2A3 | >32 | >32 | N/D[4] | N/D |

[1] the concentration of peptide (closest 2-fold dilution) required to reduce the bacterial population (CFU/ml) by 99.9%.
[2] the concentration of peptide (closest 2-fold dilution) required to reduce the bacterial population (CFU/ml) by 50%.
[3] the concentration of peptide (as measured on plot of A$_{560}$ vs peptide concentration) required to cause 50% hemoglobin release from treated RBC.
[4] not determined.

Figure 4:
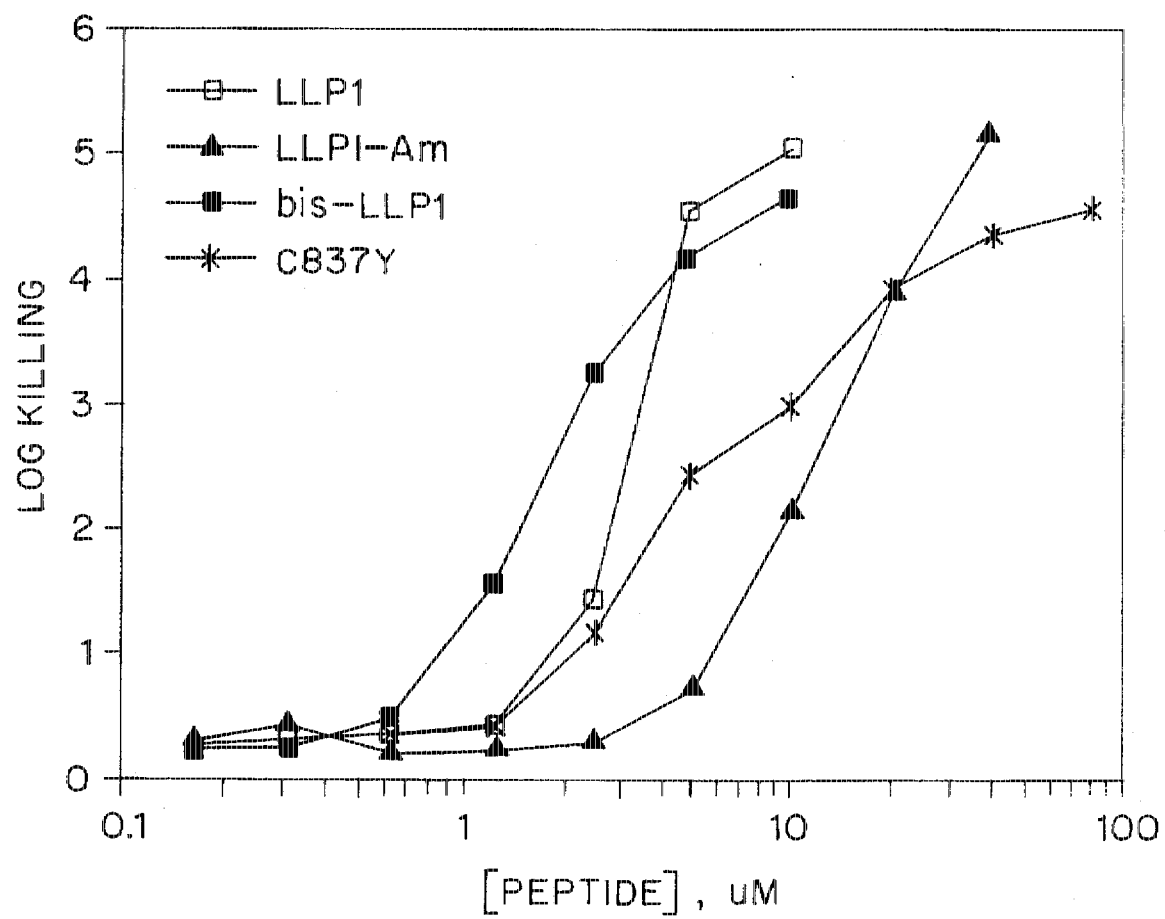
FIG. 4. shows growth inhibition of *Staphylococcus aureus* (SA) by peptides LLP1, LLP1 Am, bis-LLP1 and C837Y.

Peptide analogs which illustrate the role of the cysteine residue in LLP1 were constructed and tested (FIG. 4 and Table 8). LLP1 has one cysteine, capable of forming an intermolecular disulfide bond. Peptides were synthesized which contained alterations to the cysteine residue. LLP1-Am is a carboxyamidated peptide, in which an amide group is added to the sulfur atom of the cysteine. Peptide C837Y has a tyrosine substituted for the cysteine. The activities of these peptides as shown in FIG. 4 demonstrate that both potency and selectivity of these peptides are altered by changes which abrogate the ability of the peptide to form a disulfide bond. In another experiment, LLP1 was oxidized to ensure that its configuration was purely disulfide-linked dimer. The activity of this preparation (bis-LLP1) is higher than the parent LLP1, suggesting that the parent LLP1 preparation is a mixture of monomer and dimer and that this bis-LLP1 dimer is the highly active form of the peptide. The presence and importance of a single cysteine residue in a cytolytic peptide is a new and unique property of LLP1.

TABLE 8

Potency and Selectivity of Cysteine Substitution Analogs against *S. aureus*

| Peptide Name | MBC(μM)[1] | MBC$_{50}$[2] | Erythrocyte LD$_{50}$[3] | % lysis at 100 μM |
|---|---|---|---|---|
| LLP1 | 2–4 | 1–2 | 40 | 100 |
| C837Y | 20 | 2.5 | >100 | 10 |
| LLP1-Am | 20 | 5 | >100 | 15 |
| bis-LLP1 | 2 | 0.5 | 20 | 100 |

[1] the concentration of peptide (closest 2-fold dilution) required to reduce the bacterial population (CFU/ml) by three orders of magnitude, or 99.9%.
[2] the concentration of peptide required to reduce the bacterial population (CFU/ml) by 50%.
[3] the concentration of peptide (as measured on plot of A$_{560}$ vs peptide concentration) required to cause 50% hemoglobin release from treated RBC.

Figure 5:
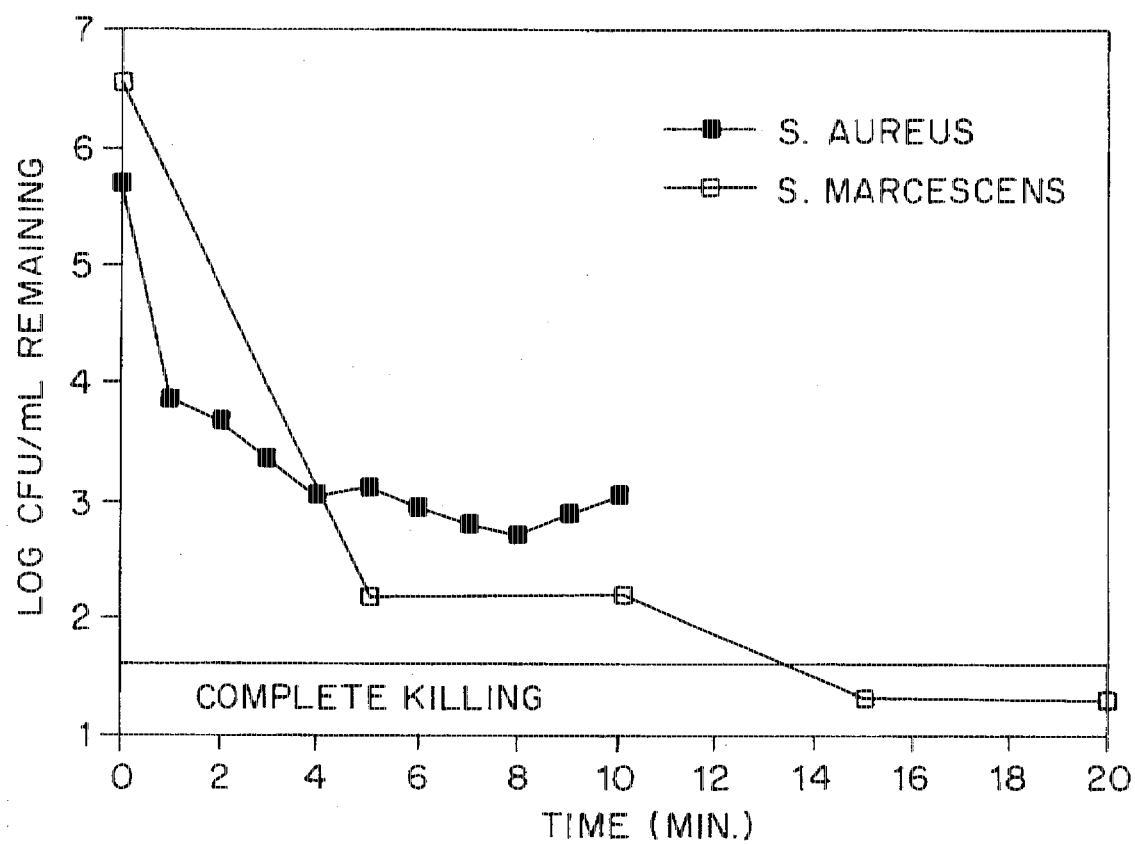
FIG. 5. shows the kinetics of lysis of *Staphylococcus aureus* and *Serratia marcescens* by peptide LLP1.

In order to determine the time-course of bacterial killing, a kinetic assay was performed. As shown in FIG. 5, over 99.99% killing is observed within one minute upon treatment of *S. aureus* with 10 μM LLP1. Similar results were obtained for *S. marcescens*, a Gram-negative pathogen. The peptide permeabilizes membranes rapidly, resulting in a 10,000-fold reduction in viability within one minute. These data indicate that the peptide's antibacterial activity is unaffected by the membrane characteristics that distinguish these two groups of bacteria.

---

We claim:

1. A peptide selected from the group consisting of:
FLIRQLIRLLTWLFSNCRTLLSRVY (SEQ ID NO:4);
LLSRVYQILQPILQRLSATLQRIREVLR (SEQ ID NO:5);
VVQGACRAIRHIPRRIR (SEQ ID NO:8); and
GACRAIRHIPRRIR (SEQ ID NO:9).

2. A peptide of claim 1 having the amino acid sequence: FLIRQLIRLLTWLFSNCRTLLSRVY (SEQ ID NO:4).

3. A peptide of claim 1 having the amino acid sequence: LLSRVYQILQPILQRLSATLQRIREVLR (SEQ ID NO:5).

4. A peptide of claim 1 having the amino acid sequence: VVQGACRAIRHIPRRIR (SEQ ID NO:8).

5. A peptide of claim 1 having the amino acid sequence: GACRAIRHIPRRIR (SEQ ID NO:9).

6. A composition comprising one or more peptides of claim 1 and a carrier.

7. A composition comprising the peptide of claim 2 and a carrier.

8. A composition comprising the peptide of claim 3 and a carrier.

9. A composition comprising the peptide of claim 4 and a carrier.

10. A composition comprising the peptide of claim 5 and a carrier.

* * * * *